(12) United States Patent
Gottfries et al.

(10) Patent No.: US 6,675,136 B1
(45) Date of Patent: Jan. 6, 2004

(54) GLOBAL METHOD FOR MAPPING PROPERTY SPACES

(75) Inventors: Johan Gottfries, Gothenburg (SE); Tudor Oprea, Gothenburg (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/462,878

(22) PCT Filed: Nov. 25, 1999

(86) PCT No.: PCT/EP99/09211

§ 371 (c)(1),
(2), (4) Date: Jan. 14, 2000

(87) PCT Pub. No.: WO00/33218

PCT Pub. Date: Jun. 8, 2000

(30) Foreign Application Priority Data

Nov. 27, 1998 (SE) ................................................ 9804127

(51) Int. Cl.[7] ......................... G06F 9/455; G06F 17/10; G06G 7/58
(52) U.S. Cl. ................................ 703/2; 703/12; 702/27
(58) Field of Search ............................. 702/22, 27, 30, 702/155; 703/2, 12

(56) References Cited

FOREIGN PATENT DOCUMENTS

| WO | 9727559 | 7/1997 |
|----|---------|--------|
| WO | 9820459 | 5/1998 |

OTHER PUBLICATIONS

Sandberg et al., "New Chemical Descriptors Relevant for the Design of Biologically Active Peptides. A Multivariate Caracterization of 87 Amino Acids", American Chemical Society vol. 41(1998) pp. 2481–2491.*

Lipinski et al., "Experimental and computational approaches to estimate solubility and permeability i drug discovery and development settings", Adv. Drug Del. Rev. (1997) vol. 23 pp. 3–25.*

Egan et al., "Outlier Deterction in Multivariate Analytical Chemical Data", Anal. Chem. (1998) vol. 70 pp. 2372–2379.*

Hellberg et al., "Peptide Quantitative Structure–Activity Relationships, a Multivariate Approach", J. Med. Chem. (1997) vol. 30 No. 7 pp. 1126–1135.*

Wison: "Computers Customize Combinatorial Libraries", Chemical and Engineering News, Apr. 27, 1998, pp 31–37.

* cited by examiner

Primary Examiner—Marjorie Moran
(74) Attorney, Agent, or Firm—White & Case LLP

(57) ABSTRACT

A computer based technique for the global investigation of property spaces is described. More particularly, a technique is described for the global investigation of chemical space, with reference to drugs, using a system comprised of molecules and descriptors that allows systematic mapping of the chemical space. The technique is used to generate a map of N-dimensional chemical space that allows one to examine, in a consistent manner with existing tools, the inner relationship between various molecules. The technique therefore allows one to investigate unexplored regions of the chemical space, avoiding redundancy, generating compounds with similar chemical information content, or to focus on subsets of the chemical space that are relevant to drug-like structures, without additional errors due to extrapolation.

49 Claims, 7 Drawing Sheets

GLOBAL METHOD FOR MAPPING PROPERTY SPACES

The present invention relates to a computer based technique for the global investigation of property spaces. More particularly, but not exclusively, the present invention relates to a computer based technique for the global investigation of chemical space, with reference to drugs, using a reference set of molecules and descriptors that allows the systematic mapping of the global chemical space. The technique, may be used, for example, to generate a global map of the multidimensional chemical space that allows one to examine, in a consistent manner, the inner relationship between various molecules.

Drug discovery is a time and resource consuming exercise. Current computer based tools allow the description of chemical spaces as local models. Many chemical fields have been targeted by approaches used, or proposed, to discover new chemicals. For example, pharmaceuticals, agrochemicals, cosmetics and perfumes, photographic materials and others have benefited from the methodology developed to assist chemical synthesis. In all these fields, central to the goal of discovery is the novelty of chemical structures, and the novelty of chemical properties. With the advent of parallel synthesis and combinatorial chemistry, large numbers of chemical compounds are now within reach for synthesis and evaluation. Crucial for the practising chemist remains the goal of prioritising, out of thousands or millions of possibilities, which compound to make next.

For a pharmaceutical or agochemical compounds, there are two main types of relevant information in a molecule, i.e. chemical and biological. Medicinal chemistry handles chemical information by identifying classes of "active molecules", then zooms in on biologically relevant information by performing various bioassays. However, in the initial stages of a research project, where little or no information is available concerning the biological target, chemical information is the only property that one can handle appropriately. Increasing the chemical information known about each compound becomes a goal of such early-phase projects, especially in the absence of active compounds.

"What's the best way to describe a molecule numerically and uniquely? What's the best way to categorise clusters of molecules? Is all this work producing results that are any better than plain old random selection?" These questions are quoted from an article by Elizabeth K. Wilson, "Computers customise combinatorial libraries", published Apr. 27 1998 in Chemical & Engineering News (pp. 31–37). This article summarises the issues discussed at the recent American Chemical Society "Diversity Symposium", organised by Robert S. Pearlman in Dallas, Tex. According to this article, the issues of molecular diversity, and of describing chemicals in an unique and relevant manner, have not been resolved. There is no general consensus as to which approach should be taken.

Molecular similarity is an ubiquitous concept that originates from the XIXth century. Attempts to rigorously define molecular similarity can be found in the book "Concepts and applications of molecular similarity", edited by Mark A. Johnson and Gerald M. Maggiora, J. Wiley & Sons, ISBN 0-471-62175-7, 1990. The impact of molecular similarity in the field of drug design, and a survey of recent advances of using molecular similarity in the pharmaceutical industry have been the aim of the book "Molecular similarity in drug design", edited by Philip M. Dean, Chapman & Hall, ISBN 0-7514-0221-4, 1995.

Molecular diversity has been the target of recent molecular similarity-based methods, in the effort to maximise the structural diversity of combinatorial and/or HTS libraries, so as to ensure the largest possible coverage of the chemical space. Molecular diversity analysis methods are surveyed in volume 7/8 of Perspectives in Drug Discovery and Design, ISSN 0928-2866, "Computational methods for the analysis of molecular diversity", edited by Peter Willet (1997).

Presently, tools to describe chemical space are used to generate local models. For example. Sergio Clementi and co-workers have described the principal properties space for a set of 40 heteroaromatic compounds in Quant. Struct.—Act. Relat. Vol. 15, pp. 108–120 (1996). In their work, Clementi et al. calculated various properties for 45 compounds running the GRID-programme, which is based on three-dimensional descriptors. Out of the resulting calculations, they have derived a set of principal properties, and have classified these compounds into ten clusters. However, they classified guanine, a biologically important heteroaromatic ring, as an "outlier" that falls outside the property space of the aforementioned GRID descriptors. One of the inherent limitations of local models is that the validity of the analysis is only as good as the dataset composition, and unique features are reflected into "outliers" which often tend to skew the statistical results and are, therefore, excluded from the analysis.

Furthermore, local models tend to be outdated, as new data are generated. This is illustrated by work performed by Svante Wold and co-workers where an initial three-dimensional property space for the 20 natural amino acids, J. Med. Chem., vol. 30, pp. 1126–1135 (1987), was extended to a five-dimensional set for 55 amino acids, Quant. Struct.—Act. Relat., vol. 8, pp. 204–209 (1989). Recently, this was further extended to a set of 87 amino acids, still using a five-dimensional property space, and published in J. Med. Chem., vol. 41, pp. 2481–2491 (1998). The 5 principal properties derived for amino acids are similar to the Hammett and Taft parameters, widely used in physical organic chemistry textbooks to correlate physico-chemical properties with molecular structures. These properties, termed "Z-scales", have been tentatively interpreted as measures of lipophilicity ($z1$), size/polarizability ($z2$), polarity ($z3$), while the fourth and fifth scales ($z4$ and $z5$) were more difficult to interpret. This work has extended the principal property space represented by the twenty natural amino acids with an additional set of 67 non-coded amino acids, some of them explicitly synthesised to cover unique properties. However, these Z-scales remain valid only for amino acids, and further synthesis of novel structures would lead to revaluation of the principal properties, and of the "Z-scores" for individual amino acids.

Current computer based technology allows the end-user to generate, in silico, extremely large numbers of compounds. For example, Tripos Inc. and Silicon Graphics have announced that they in a joint project have created a virtual library consisting of 100 billion molecules, using a "Space-Crunch" technology.

Tripos' software ChemSpace™ yields "all possible molecular products resulting from given reactions, allowing chemists to start travelling with confidence over large expanses of the chemical universe". This software promises a structural description of the chemical universe/space, based on single compounds and within certain limits. Chemspace™ is a searchable database consisting of billions of compounds synthesizable from known reactions and available reagents. This method includes tools to navigate in the database. However, the database represents only a subset of the chemical space, limited by the type of chemical reactions and reactants provided in "SpaceCrunch". This stepwise manner to map chemical space has been, so far, the only alternative to true chemical space navigation.

From all the above, one can observe that there is a considerable need to navigate in the chemical space.

The present invention addresses the disadvantages discussed above and allows one to generate a global model that includes, and can specifically analyse, (e.g. heteroaromatic compounds (vide infra)) without the risk of extrapolation or outlying behaviour, given that the raw data are correct.

It is an object of the present invention to provide a computer based method to investigate any property space, e.g. a chemical and/or biological space, based on a set of objects (structures), e.g. chemical compounds and/or biologically relevant observations, and a set of variables, e.g. chemical descriptors and/or biologically relevant parameters, that allow a global systematic description of that given property space.

It is a further object of the present invention to provide a computer based method to investigate the chemical space in a global manner, thus avoiding redundancy and providing ways to explore novel regions of the chemical space, without the need for extrapolation.

Viewed from one aspect the present invention provides a method of mapping a target object of a target type into a target hyper-volume within a model in N-dimensional space containing a plurality of objects, each object in said model having an associated set of variables defining its position within said N-dimensional space, each variable having a maximum and minimum value within said model, said method comprising the steps of:

storing core object data representing a plurality of core objects of said target type within said target hyper-volume, said target hyper-volume being positioned spaced away from said maximum and minimum values of said variables;

storing satellite object data representing a plurality of satellite objects not of said target type positioned outside of said target hyper-volume;

determining from characteristics of said target object a position of said target object within said hyper-volume using the same evaluation criteria as used for said core objects and said satellite objects;

positioning said target object within said model relative to said core objects and said satellite objects in accordance with said determined position; and generating a user output indicative of said relative position of said target object.

The invention recognises that when seeking to map a target object into a target hyper-volume, improved results can be achieved if the model being used includes not only core objects within the target hyper-volume but also satellite objects positioned outside of the target-hyper volume. Whilst the satellite objects may be very different to the target objects of interest, the presence of the satellite objects within the model provides the model with a much higher degree of generality and the ability to cope with target objects that are relatively different from the core objects. In contrast to the global model allowed by the invention, a local model of the type discussed above has the ability to cope with the target objects that are of a similar nature to the known objects within the model but is ill-equipped to provide meaningful results when the target object becomes relatively different from the objects already within the local model. For this reason, local models are limited by the type of input data, and are not suitable for the mapping of different types of target object. Furthermore, a relationship between different objects that may be identified with a global model may not be found when those objects are separately modelled within their local individual models.

The present invention seeks to avoid the problems of the prior art by explicitly including molecules with extreme properties in the dataset. These molecules with extreme properties play the role of satellites and allow the principal property values to remain fixed during the analysis. Thus, the present invention provides a consistent method to map the chemical space, not only for amino acids or heteroaromatic compounds, but for any type of chemical compounds considered within the set of conventions described below.

From a mathematical perspective, the use of satellite objects within the model but outside of the target hyper-volume has the advantage of providing a more flexible and globally representative set of unit vectors defining the N-dimensional space against which a particular target object may be mapped. It is surprising that mapping of a target object into a target hyper-volume, e.g. a potential pharmaceutical into the hyper-volume of known pharmaceuticals, is improved by deliberately incorporating satellite objects within the model that have a very different character to the target objects of interest within the target hyper-volume. One way of understanding this improvement is to view the satellite objects as providing the ability to interpolate the position of the target object within the model whereas a local model may require much less accurate extrapolation of the position of a target object if that target object is not very similar to the objects already within the local model.

It will be appreciated that the modelling technique of the invention could be applicable to many different fields. However, the invention is particularly well suited to models in which the objects are chemical structures and the variables are chemical variables. More particularly, the technique is highly beneficial when the target type is pharmaceutically active chemical structures and the core objects include known pharmaceuticals whilst the satellite objects are not pharmaceutically active.

In order to derive the unit vectors representing the component axis within the N-dimensional space, it has been found beneficial to use principal component analysis to determine eigen-vectors to serve as these component unit vectors. Principal component analysis provides a way of identifying the best vectors for representing an N-dimensional space without redundancy that would introduce undesirable complexity.

A target object to be mapped will also be subject to principal component analysis in the sense that it will be positioned within the model using the value of its co-ordinates in the N-dimensional space whose component unit vectors are determined using principal component analysis.

If a target object is found to lie outside of the target hyper-volume then it is sometimes useful to add that target object to the model to serve as a satellite object. Whilst the position of the target object outside of the target hyper-volume makes it more difficult to interpret its relationship with other objects within the model, its addition to the model can to have the advantage of improving the degree of global applicability of the model and may also serve to indicate a relationship with some future target object to me mapped to the model.

Many different variables and maximum and minimum values can be chosen for the model. However, in the case of a model seeking to identify pharmaceuticals, particularly useful properties are molecular weight, molecular size, molecular flexibility, molecular rigidity, formal negative charges, formal positive charges, the ability to accept hydrogen bonds, the ability to donate hydrogen bonds, lipophilicity and atomic polarisabilities as described by variables related to the aforementioned properties (vide infra). It will be appreciated that different combinations of these variables can be used in combination with other variables if so desired. Calculated molecular refractivity and molecular volume may also be used as alternatives to or in addition to molecular size.

Viewed from another aspect the present invention provides an apparatus for mapping a target object of a target type into a target hyper-volume within a model in N-dimensional space containing a plurality of objects, each object in said model having an associated set of variables defining its position within said N-dimensional space, each variable having a maximum and minimum value within said model, said apparatus comprising:

a memory for storing core object data representing a plurality of core objects of said target type within said target hyper-volume, said target hyper-volume being positioned spaced away from said maximum and minimum values of said variables and for storing satellite object data representing a plurality of satellite objects not of said target type positioned outside of said target hyper-volume;

determination logic for determining from characteristics of said target object a position of said target object within said hyper-volume using the same evaluation criteria as used for said core objects and said satellite objects;

positioning logic for positioning said target object within said model relative to said core objects and said satellite objects in accordance with said determined position; and a user output device for generating a user output indicative of said relative position of said target object.

Viewed further a further aspect the invention provides a method of forming a model in N-dimensional space containing a plurality of objects and a target hyper-volume into which target objects are to be mapped, said method comprising the steps of:

selecting a set of variables defining said N-dimensional space;

selecting maximum and minimum values for said variables;

selecting a representative set of core objects within said target volume;

selecting a representative set of satellite object outside of said target volume; and iteratively testing and altering said model to obtain a set of variables, maximum and minimum values, core objects and satellite objects that span said N-dimensional space and allow target objects to be mapped to within said target volume.

Viewed from a still further aspect the invention provides a carrier medium carrying a computer program product for mapping a target object of a target type into a target hyper-volume within a model in N-dimensional space containing a plurality of objects, each object in said model having an associated set of variables defining its position within said N-dimensional space, each variable having a maximum and minimum value within said model, said computer program product providing the processing steps of:

storing core object data representing a plurality of core objects of said target type within said target hyper-volume, said target hyper-volume being positioned spaced away from said maximum and minimum values of said variables;

storing satellite object data representing a plurality of satellite objects not of said target type positioned outside of said target hyper-volume;

determining from characteristics of said target object a position of said target object within said hyper-volume using the same evaluation criteria as used for said core objects and said satellite objects;

positioning said target object within said model relative to said core objects and said satellite objects in accordance with said determined position; and generating a user output indicative of said relative position of said target object.

It will be appreciated that the carrier medium for carrying the computer program could take many different forms. Examples of carrier media include magnetic discs, optical discs, memory integrated circuits and the like, but also include distribution media such as distribution via a telecommunications system, e.g. the downloading of computer software from a telecommunications medium such as the internet.

Embodiments of the invention will now be described, by way of example only, with reference to the accompanying drawings.

Figure 1:
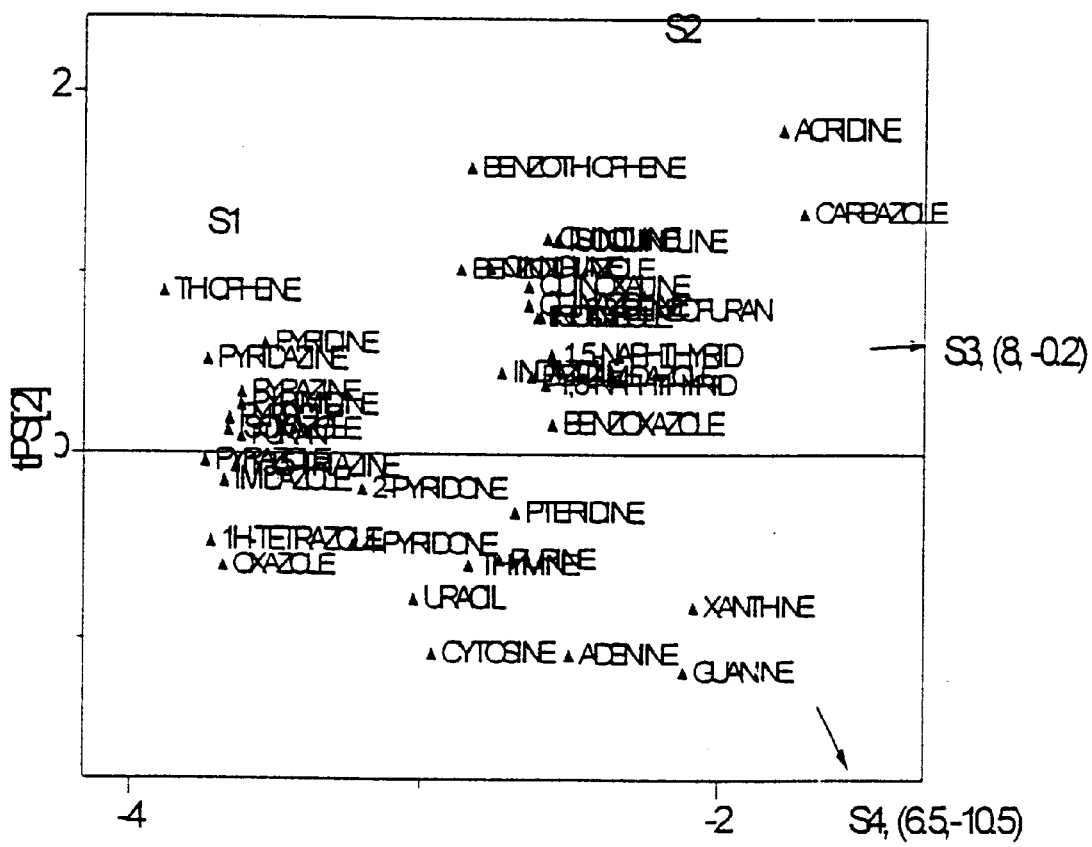
FIGS. 1 and 2 are example portions of global maps of chemical space.

As used herewithin, the following words and expressions are intended to have the following meaning:

anchor object:objects situated at the corners of a region of the global property space that is user-defined, for example those that can be defined by the "Pfizer's rule of 5" for the oral absorption of drugs.

convergent: tending to move toward one point or to approach each other core: the central, innermost, or most essential part of anything.

core object: an object that is positioned globally inside the hypervolume of interest, e.g., an object structure situated inside the chemical space of drug-like compounds, where this core object possesses average and/or typical properties related to the drug-like space and/or the object is a marketed drug structure.

global: covering the whole of a group of items, where the group of items could be, e.g., all the organic chemicals composed of C, H, N, O, S, P and halogens with a molecular mass of maximum 1500.

satellite: anything that depends on, accompanies, or serves something else.

satellite object: an object that is positioned globally outside the hypervolume of interest, e.g., a satellite structure situated outside the chemical space of drug-like compounds, where this satellite possesses extreme properties related to the aforementioned drug-like structures.

Briefly, the process of forming and using a model can comprise the following steps:

choosing and/or defining the property space
defining the extreme values for the set of relevant properties
choosing a representative set of satellite and core objects
obtaining a convergent set of rules
modelling
outputting a map The following describes a computer based method for global navigation in property spaces, particularly in the chemical space, hereinafter referred to as ChemGPS (Chemical Global Property System). ChemGPS allows one to investigate unexplored regions of the chemical space, avoids redundancy, generates compounds with similar chemical information content. or focuses on subsets of the chemical space that are relevant to drug-like structures, without additional errors due to extrapolation.

Current tools allow description of chemical spaces as local models, based on (i) a set of existing and theoretical molecules, (ii) a set of chemical descriptors and (iii) multivariate analysis. We have surprisingly found a computer based method that maps the global chemical space whilst allowing the reuse of many existing tools. In particular, the present system makes it possible to globally investigate the chemical space that is relevant to drug-like compounds. This is accomplished using a model that includes a set of rules and a set of "satellite" molecules, i.e. molecules having extreme properties, that are intentionally placed outside the property space of interest (target hyper-volume), along with other chemical structures that would not normally be deemed relevant for this problem. The chemical descriptors that are used may, or may not, be relevant to biological space.

The present technique in general allows one to systematically and consistently investigate any property space, including the chemical space.

The purpose of the present example technique is to overcome the limitations of the earlier approaches and to generate a global model of the chemical space that is relevant to drug-like compounds, using mapping convention, hereby termed chemography. Analogous to the Mercator convention, widely used in geography, chemography consists of a set of conventions used to navigate in chemical space. These conventions include a set of filtering properties, and a list of molecules that are chosen to cover these properties.

For the drug-related chemical space, these filtering properties include, but are not limited to: size and molecular weight, flexibility, rigidity, negative and positive formal charges, the number of hydrogen bond donors and acceptors, lipophilicity and polarizability. Other filtering properties that may be relevant, and also within the scope of the present technique, are pKa, logD and pharmacophoric patterns relating chemicals to a given receptor, but also chemical fingerprints such as those obtained using the Daylight CIS software or the Tripos. Inc software.

For drug-like molecules, the chemical space can be set by the following rules (maximum and minimum values for variables: molecular weight below 1500 daltons; calculated octanol/water partition coefficient between −20 and +20; up to 50 non-terminal rotatable bonds; up to 50 hydrogen bond donors and acceptors; up to 6 net formal charge units (−6 to +6); and up to 30 rigid centers. For the purpose of illustration, the chemical space comprises only the following elements: carbon, hydrogen, oxygen, nitrogen, sulfur, phosphorus and halogens. The above rules are used to filter the type and kind of compounds included. However, they do not represent the final set of descriptors, since the chemical space can be extended.

For example, the definition of the chemical space relevant to drug properties can be extended by including other chemical elements (transition metals, boron, alkaline metals, etc.), and/or other properties referring to descriptors such as pKa, LogD, and/or Spartan-calculated descriptors, and also by including methods that describe chemical fingerprints like those from Daylight or Tripos, and ISIS keys, and are all within the scope of the present technique.

Two types of molecules (objects) are also considered as an integral part of the present technique: "core" and "satellite" objects. Core objects comprise a representative set of e.g. pharmaceutical and/or any other relevant chemicals, chosen according to the filtering properties. Satellite objects, that represent a crucial part of the present technique, are molecules chosen to represent extreme filtering properties, and are intentionally placed outside the drug-related property space (target hyper-volume).

The final step of the method refers to the use of the present technique for mapping new objects. This includes estimation of chemical properties via computer calculation of descriptors and subsequent PCA of any set of objects. Derived from multivariate analysis, the new set of latent properties is consistent for each compound, and is valid within the rules set by the afore-mentioned chemographic convention. The map is illustrated via score plots for each significant latent property, where each score is obtained using prediction based on the converged ChemGPS model. The ChemGPS method allows one to avoid the limitations of local models, and provides the tools to navigate in the chemical space via interpolation, in contrast to "external prediction", which is performed via potentially unreliable extrapolation from local models.

For the purpose of illustration, we provide the following list of software methods to calculate descriptors relevant for chemical properties: Sybyl (from Tripos Inc, St.Louis, Mo.); Spartan (from Wavefunction, Irvine, Calif.); TSAR (from Oxford Molecular, Oxford, England); GRID (from Peter Goodford, Oxford, England); Cerius2 (from Molecular Simulations, Inc., San Diego, Calif.); Moloconn Z (Hall Associates Consulting, Quincy, Mass.); CLOGP (Biobyte, Claremont, Calif.); ACDLogD (ACD Labs Inc, Toronto, Canada); Hybot, 5.0, Raevsky & Grigorev, Moscow, Russia etc. Based on the above list of descriptors, one can perform data compression using artificial neural networks (with a number of methods, e.g., the Kohonen self-organizing map), and/or data reduction using principal component analysis (PCA), by ways of using the SIMCA software (from Umetri, Umeå, Sweden), or Unscrambler (from CAMO AS, Oslo, Norway), or Matlab (Comsol, Stockholm, Sweden). The preferred way of the invention is to perform data reduction using PCA, as implemented in the Simca package.

The present technique represents a chemographic system that, for example, can be applied to the pharmaceutically relevant chemical space. It could, however, be applied to any other part of chemistry, e.g. agrochemicals, perfumes, dyes and pigments, polymers, etc., by appropriate use of the filtering properties that are relevant to that particular field of chemistry, and by an appropriate choice of core and satellite objects that are relevant to that area of chemical space. Satellite objections that are relevant to a certain region of the chemical space need not be informative for other regions.

The present technique can be viewed as a computer based method to generate a global model of any property space that is deemed of interest, and can be implemented in a so plurality of property spaces. By using a set of rules and objects, described above for the chemical space as "chemography", one can generate a set of filtering properties and a list of satellite and core objects that best describe that property space. Illustratively, the property space may be the chemical space relevant to drug-like compounds. The present technique can thus provide a powerful tool or method for navigating in the chemical space that includes any desired physical and/or chemical properties, but has particular utility for the discovery of pharmaceutical drugs. Referring to the filtering properties that are relevant to the drug space, a list exemplifying such properties is given below:

M.W.: This descriptor is the molecular weight of each compound, expressed in daltons.

SIZE: This descriptor is a rough estimate of molecular size, and adds 1 point for every four non-hydrogen atoms. This is based on the rough estimate that a 500 dalton compound has 40 heavy atoms. This complements M.W., since third (or higher) period elements contribute significantly to M.W., without a similar increase in the size of the molecule.

FLEXI: This is a count of all non-terminal rotable bonds and/or repeating units such as (C=C—C). The molecule may include rigid units positioned between the non-terminal rotatable bonds. This descriptor also adds "n" for each non-rigid ring with n=N−4−x/2, where N is the number of bonds in a ring, x is the number of atoms in other rings (spiro counts as 1). Amides and esters are ignored.

RIGID: This is a count of all rigid structures such as rings, amides, ester groups, carboxylates, nitro groups, etc. Additionally, 1 point is given for each fused ring.

QMINUS: This is a count of all formal negative charges only, such as carboxyl groups, sulfate groups, phosphate groups, e.t.c, and all other groups that can be deprotonated at physiological pH.

QPLUS: This is a count of all formal positive charges only, such as amines, amidines, guanidines, e.t.c., and all other groups that can be protonated at physiological pH.

HBACC: This is a count of all oxygen and nitrogen atoms that can accept hydrogen bonds.

HBDON: Counts Q—H and N—H moieties only. Carboxyl groups are ignored, because they are ionised.

LIPO: This descriptor is based on the CLOGP software (from Biobyte, Claremont, Calif.) to estimate the partition coefficient between n-octanol and water. Other logP calculators such as Acdlogp (Advanced Chemistry Developments, Toronto, Canada) are included whenever CLOGP fails.

POLAR: This descriptor is a sum of atomic polarizabilities, based on the following empirical polarizability scale: H 0.35; C 1.3; N 1.0; O 0.6; S 2.9; P 3.3; F 0.4; Cl 2.3; Br 3.2; I 5.0.

Based on the above filtering properties, a number of molecules that are within certain limits are included in a chemical database, for example an ISIS database. Filtering property limits (i.e. maximum and minimum variable values) are set by the end-user, and can be modified according to the purpose of the navigational tool. For drug-like molecules, one can for example assume the following limits; maximum M.W. 1500 daltons, LIPO between −10 and +20, maximum FLEXI 50, up to 20 hydrogen bond donors and acceptors (HBDON/HBACC), up to 6 net ionic charges (QMINUS and QPLUS), and up to 30 rigid centers (RGID). In this illustrative example, only S, N, O, P and X were considered as heteroelements (besides C and H).

The choice of core objects is performed according to the initial set of filtering properties, and the following drugs can for example be chosen to be diverse, according to the above filter scheme. For example, propranolol, secobarbital, trandolapril, ibuprofen, tolbutamide, caffeine and omeprazole represent a set of pharmaceutically, and chemically distinct set of drugs that may be included in the "core" set of objects.

Satellite objects consist of a list of molecules chosen to represent chemical structures that have extreme values according to the filtering properties. They are analogous to the global positioning satellite (GPS) system, because they are intentionally situated outside the chemical space to provide interpolation (not extrapolation) abilities to any model derived using these structures. For example, acetyldigitoxin, a cardiovascular drug, represents a satellite (M.W.=806.98; SIZE=14; FLEXI=8; RIGID=10; QMINUS=QPLUS=0; HBACC=14; HBDON=4; LIPO=2; POLAR=64.3), in a similar manner to vinblastine. an anti-cancer agent (M.W.=813; SIZE=15; FLEXI=8; RIGID=14; QMINUS=0; QPLUS=2; HBACC=10; HBDON=4; LIPO= 3.69; POLAR=90.2). For property extrema not well-illustrated by drugs, additional compounds can be included, such as tetraphenyl-adamantane (M.W.=440.63; SIZE=8; FLXI=4; RIGD=8; QMINUS=QPLUS=HBACC= HBDON=0; LIPO=9.63; POLAR=55.4), and the arginine tetrapeptide (M.W.=654.86; SIZE=11; FLEXI=34; RIGID= 11; QMINUS=−1; QPLUS=5; HBACC=5; HBDON=16; LIPO=−10; POLAR=67.7). At the other end of the property space, compounds such as carbon tetrachloride (M.W.= 153.32; SIZE =1; FLEXI=0; RIGID=1; QMINUS=QPLUS= HBACC=HBDON=0; LIPO=2.83; POLAR=10.1), and urea (M.W.=60.05; SIZE=1; FLEXI=0; RIGID=1; QMINUS= QPLUS=0; HBACC=1; HBDON=2; LIPO=−2.11; POLAR=5.3), can also be included.

The combination of satellite and core objects, selected using a pre-defined filtering scheme, define a convention by which manner to comprehensively describe any property space. Without this approach, models are limited by their dataset in their ability to properly represent the property space of interest. The presence of satellite and core objects stabilises the model, and the resulting "scores" are applicable to all areas of the property space of interest (target hyper-volume), as long as this space is covered by the satellite system. In an analogy to the Global Positioning System (GPS), the present technique allows one to establish where New England is on the world map, in relationship to Sweden and India, whereas other approaches are only able to provide local maps of the aforementioned regions. By introducing satellite objects with an N-dimensional model, we have surprisingly been able to provide an improved mapping technique for the chemical space.

To further illustrate the versatility of the present technique, we also introduce the concept of "anchor" objects. Anchor objects are molecules situated at the corners of a region of the drug space that is defined by Pfizer's "rule of 5". This rule has been empirically derived by a computer analysis of known drugs, as described by Christopher A. Pfizer and co-workers in Adv. Drug Delivery Rev., vol. 23, pp. 3–25 (1997). The "rule of 5" is focused on drug permeability and oral absorption, and by introducing anchor objects, one is capable of using the chemographic tool to focus on drug-like molecules that show good pharmacokinetic properties. According to Pfizer's "rule of 5", LIPO and HBDON are between 0 and 5, HBACC is between 0 and 10, and M.W. has a maximum of 500. For example, 1,2,4,5 tetrathiane (C2H4S4). (M.W.=153.82; SIZE=1; FLEXI=2;

RIGD=1; QMINUS=QPLUS=HBACC=HBDON=0; LIPO=1.02; POLAR=15.84), and bis-methyldisulfanyl-methane (M.W.=172.36; SIZE=2; FLEXI=4; RIGID= QMINUS=QPLUS=HBACC=HBDON=0; LIPO=2.19; POLAR=18.8) are virtual anchor points that constitute representative objects situated in an extreme region, as defined by Pfizer's "rule of 5".

Figure 4:
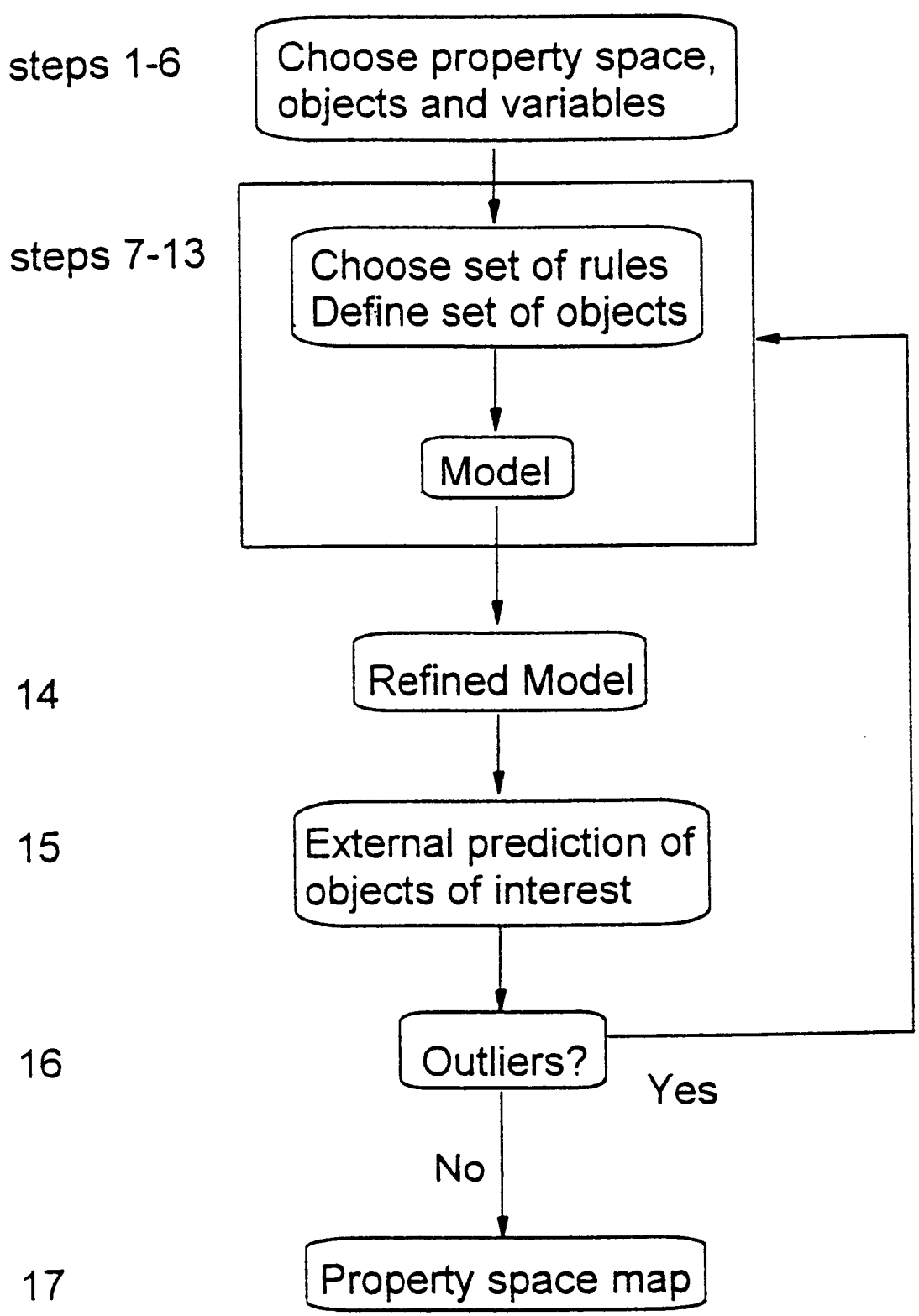
FIGS. 4, 5 and 6 are flow diagrams illustrating the operation of one embodiment of the invention.
Figure 5:
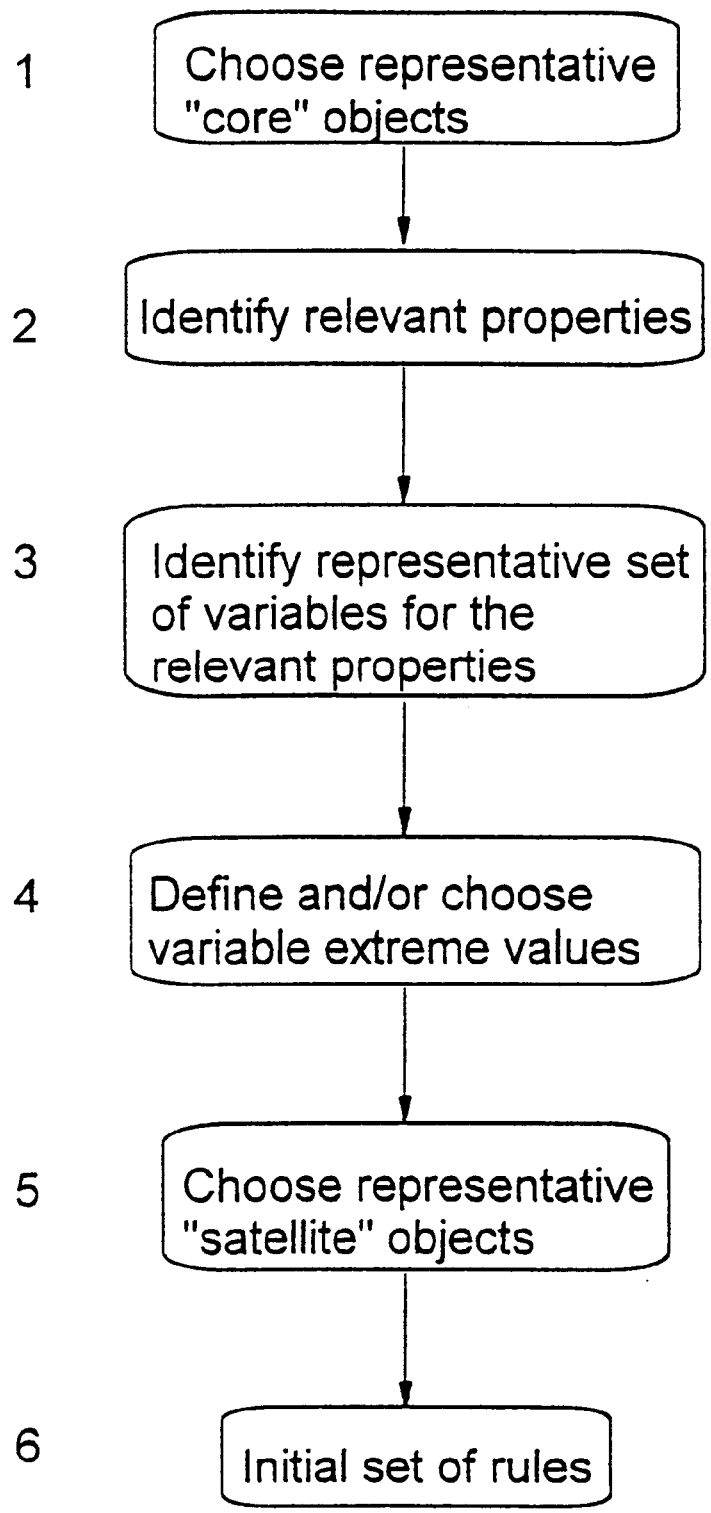
Figure 6:
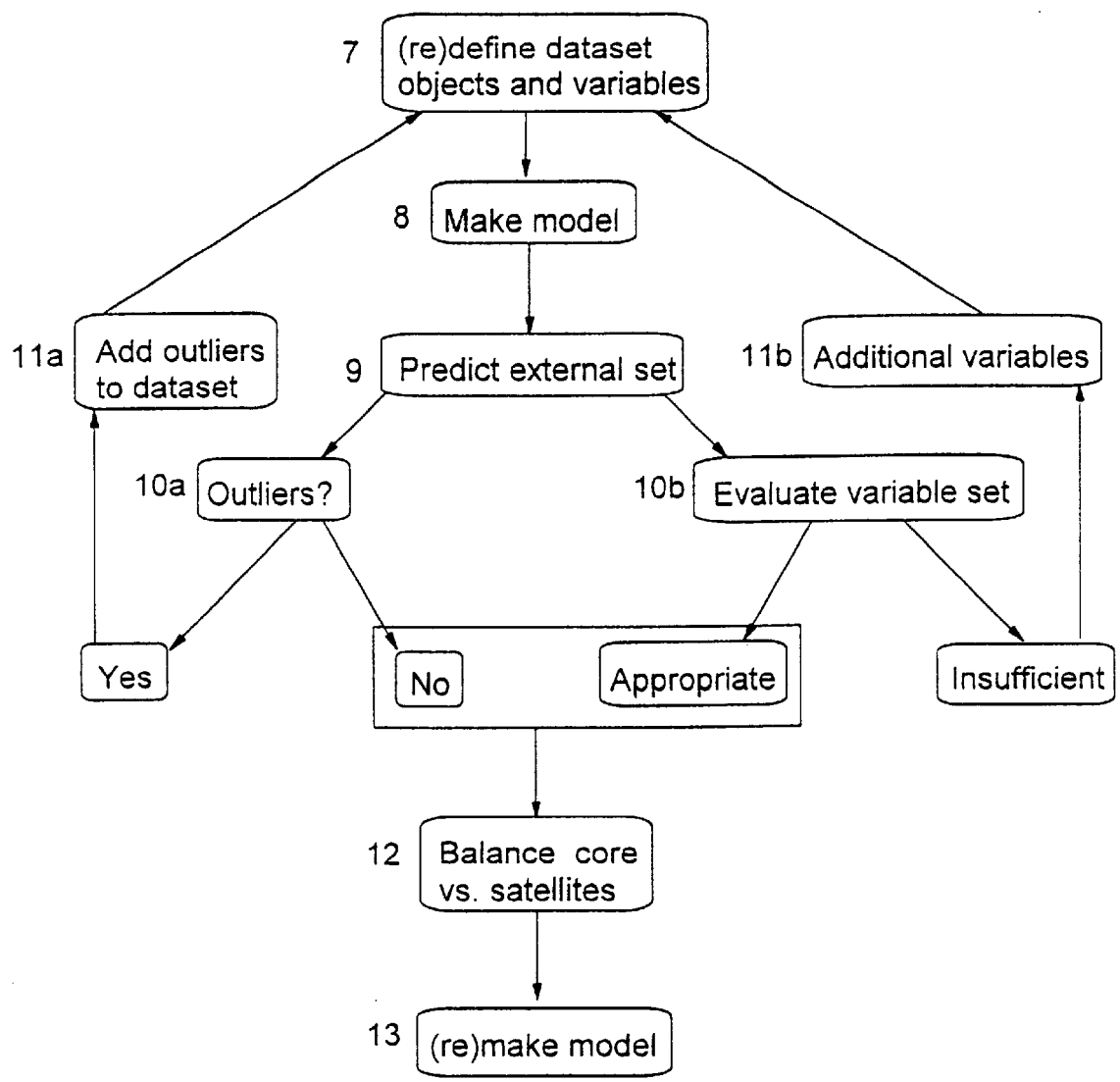

A method of forming a model in accordance with the present technique is shown in flowchart form in FIGS. 4 to 6. FIG. 4 is a general scheme of carrying out the present technique, and includes several steps explicitly shown in more detail in FIG. 5 and FIG. 6, respectively. FIG. 5 is a detailed description of steps 1 to 6, that are explained below. FIG. 6 is a detailed description of steps 7 to 13, that are also explained below.

The initial steps in the present technique are to choose the property space, with its objects and variables (see FIG. 5). These steps would take the user to a crude model that can be used to map objects in the property space. However, steps 7 to 16 are recommended before proceeding to step 17. Steps 7 to 13 of the present technique are to refine the initial model from steps 1 to 6, as shown in FIG. 6.

The process of the present technique in the drug-like property space comprises the following steps:

Step 1
is to choose a set of "core" objects that are representative for the area of interest, e.g. drug-like molecules.

Step 2
is to identify a set of relevant properties for the core objects identified in step 1, for example lipophilicity and size for drug-like compounds.

Step 3
is to identify variables that, in a meaningful way, describe the properties that are found to be relevant in step 2, for example calculated octanol/water partition coefficient (CLOGP) to describe lipophilicity, and calculated molecular refractivity (CMR) to describe molecular size.

Step 4
is to define and/or choose the range of the variables identified in step 3. Extreme values are chosen for each variable in this step. For example, values between −10 and +20 could be chosen for CLOGP, and values between 1 and 30 could be chosen for CMR.

Step 5
is to choose a representative set of satellite objects. Satellites are existing or hypothetical objects that correspond to extreme values of the chosen variables. For example, a large (CMR=20) and very lipophilic compound (CLOGP=10) could be seen as a satellite in the drug space.

Step 6
is to define an initial set of rules, i.e. an initial set of variables and an initial set of core and satellite objects.

Step 7
is to refine the set of rules chosen in step 6, if these are not satisfactory according to conditions described in steps 10a and 10b.

Step 8
is to generate a model based on the dataset constructed in steps 6 and 7, by ways of using e.g., principal component analysis (PCA) that identifies eigen-vectors within a the property space.

Step 9
is to use the model from step 8 to predict values, e.g. the PCA scores, for the variables chosen in steps 6 and 7 for an external set of objects (one or more target objects to be positioned within the model). The external set typically constitutes of a set of objects that the user may find of interest to his particular problem. For example, a set of chemical reactants (objects) may be submitted to variable prediction to estimate their molecular properties in comparison to drug-like properties.

Step 10
consists of two parts: step 10a detects the presence of outlying objects predicted in step 9. If such outliers are detected, then proceed to step 11a. Step 10b evaluates the variable set. This is where the appropriateness of the variable set for the problem of interest is re-evaluated. If the chosen variables are not appropriate, then proceed to step 11b. If neither step 11a or 11b are required, then proceed to step 12.

Step 11
consists of two parts: step 11a is the process of adding outliers to the dataset, since they are likely to be satellites. If these outliers (or objects with equivalent variable values) are already present in that dataset, they should not be included in the dataset since an overrepresentation of satellites in the model is not recommended (see step 12). Step 11b is to define additional variables in order to obtain a comprehensive description of the property space defined in step 2. For example, polarity may be relevant to drug-like properties, in addition to lipophillicity and size. In this case, new variables describing polarity (e.g., electronegativity) should be added to the variable set, and representative satellite structures should be included.

Step 12
is performed to balance the composition of the dataset, regarding the number of core and satellite objects, due to statistical reasons. For example, an overrepresentation of either type of objects may lead to a skewed final map (see step 17).

Step 13
is to make (or remake) the model, according to the existing set of rules (objects and variables), by way of using, e.g., PCA.

Step 14
is reached when the model has already been refined, and a satisfactory set of objects with corresponding relevant variables, have been selected.

Step 15
is to use the refined model from step 14 to predict variable values, e.g. the PCA scores, for a new external set of objects, or for the same set of objects as in step 9.

Step 16
consists of looking for outlying objects. If, at this stage, outliers are detected, then step 11a should be performed, and the process should be reiterated from step 7. Otherwise, proceed to step 17.

Step 17
is the construction of the property space map, using, e.g., PCA score plots. The map is ready to use for navigating in that particular space.

Step 18
is the use of the map obtained in Step 17 to assign map scores (or co-ordinates) for new objects (target objects). This step includes estimation of object properties via computer calculation of descriptors and subsequent PCA. Score values, that can be displayed as score plots, are then obtained for each significant latent property via prediction. Each score value is obtained using prediction based on the converged model (i.e. using the same evaluation techniques).

The present technique can be used to generate a map of the multidimensional chemical space that allows one to examine, in a consistent and conventional manner, the inner relationship between various molecules. The present technique can therefore be used for the following:

Use for selection of reactants and molecular diversity analysis, prior to combinatorial chemistry and/or parallel synthesis.

Use for compound (product) clustering and evaluation of molecular similarity, prior to structure-activity relationship studies.

Use for database analysis and comparison of chemical information.

Use for defining subregions of the property space, via "anchor" objects, that can be used to visualize the same region.

Use of the map of the chemical space to assign molecular similarity and/or diversity.

Use of the map to predict the probability of a given structure to have good oral absorption if administered per ostium.

Use of map co-ordinates as descriptors for QSAR, QSPR and other mathematical models relating chemical structure to macroscopic properties.

Use of map co-ordinates as unique identifiers for storing molecules in a chemical database, e.g. similar to the CAS number or to the unique SMILES string, but having the advantage that it incorporates information relating to chemical properties.

Use of the ChemGPS system to predict drug-related properties for novel compounds.

Use of the ChemGPS system for discriminating "drug-like" vs. "non-drug-like".

Some possibilities uses foreseen for the described system, will be exemplified by its performance on rigid heterocyclic compounds in comparison to GRID/GOLPE approach as presented by Clementi et al., Quant. Struct.—Act. Relat. Vol. 15, pp. 108–120 (1996) and as first discussed below.

Reference should be made to the examples described Clementi et al., Quant. Struct.—Act. Relat. Vol. 15, pp. 103–120 (1996).

GRID is a program that calculates interaction energies of given probes with the molecules.

The following GRAD probes were used:

N1 (neutral flat NH) as in main chain amide
N:=(sp2 N with lone pair) as in Triptophan, Histidine
N1+(sp3 amine NH cation) as in Arginine, Lysine, Histidine
OH (sp2 hydroxy group) as in Tyrosine
O (sp2 carbonyl oxygen) as in main chain amide
O1 (sp3 hydroxy group) as in Serine, Threonine
COO— (carboxylate) as in Asparate, Glutamate
CONH2 (amide group) as in Asparagine, Glutanmine
Amidine as in Arginine
Additional volumes and surfaces were calculated for hydrophobic and hydrophilic probes (4 descriptors).

Four principal properties were obtained using these calculations. Guanine was excluded as an outlier, and for the rest, the results are interpreted below:

PP1: negative means hydrophobe, positive means hydrophile (40% contribution);

PP2: describes the H-bond ability, and differentiates acceptors (azoles, azines) from slight donors (diazoles, pyridones) (16% contribution)

PP3: separates shape & hidrophobicity: monocyclic (negative) and bicyclic (positive). The carboxylate probe determines the relative positions of the compounds (16% contribution);

PP4: mulitple amidine interactions; differentiates chalcogen [O, S] containing systems from those with nitrogen (10% contribution).

This lead to 10 groups of heteroaromatic compounds. Best representatives are given below: 1A: pyrrole; 1B: thiophen; 1C: indole; 1D: benzothiophene; 2E: pyridine; 3G: imidazole; 4F: quinoline; 4H: benzimidazole; 5I: uracil; 5J: purine Note: Aniline, benzene, phenol, naphthalene and thiazole were not included in the clustering scheme.

Clementi et al., Quant. Struct.—Act. Relat. Vol. 15, pp. 108–120 (1996), have thus calculated several 3-D interactions using different property probes, i.e. calculating the energy interaction from every grid-point between a methyl or NH4+ etc. moiety (the probe) for every training set molecule for every grid-point with e.g. 0.5 Å resolution (the GRID approach by P. Goodford). The resulting data-matrices, containing >50 000 data-points, were then subjected to chemometric calculations similar to those performed by us. By doing this they created a local model that well describes the chemical space of rigid heterocyclic compounds (n=45 for their training set).

Example of ChemGPS

We initially performed database searches in "comprehensive medicinal chemistry", a publicly available database, and identified an initial set of 128 molecules. These chemicals were substances registered for medical use and were defined as the initial set of "core" objects (Step 1).

The following properties were identified as being relevant for these drugs: mass, size, lipophilicity, charge, flexibility, hydrogen-bond donor and acceptor ability, and polarizability (Step 2).

The following variables were identified (Step 3):

M.W.: This descriptor is the molecular weight of each compound, expressed in daltons.

SIZE: This descriptor is a rough estimate of molecular size, and adds 1 point for every four non-hydrogen atoms. This is based on the rough estimate that a 500 dalton compound has 40 heavy atoms. This complements M.W., since third (or higher) period elements contribute significantly to M.W., without a similar increase in the size of the molecule.

FLEX: This is a count of all nonterminal rotatable bonds and/or repeating units such as (C=C—C). This descriptor also adds "n" for each non-rigid ring with n=N−4−x/2— where N is the number of bonds in a ring, x is nr of atoms in other rings (spiro counts as 1). Amides and esters are ignored.

RIGID: This is a count of all rigid structures such as rings, amides, ester groups, carboxylates, nitro groups, etc. Additionally, 1 point is given for each fused ring.

QMINUS: This is a count of all formal negative charges only: carboxyls, sulfates, phosphates, etc, and all other groups that can be deprotonated at physiological pH.

QPLUS: This is a count of all formal positive charges only: amines, amidines, guanidines, etc., and all other groups that can be protonated at physiological pH.

HBACC: This is a count of all oxygens & nitroges that can accept hydrogen bonds.

HBDON: Counts O—H and N—H moieties only. Because carboxyls are ionized, they are ignored.

LIPO: This descriptor is based on the CLOGP software (from Biobyte, Claremont, Calif.) to estimate the partition coefficient between octanol and water. Other LogP calculators such as ACDLOGP (Advanced Chemistry Developments, Toronto, Canada) are included whenever CLOGP fails.

POLAR: This descriptor is a sum of atomic polarizabilities, based on the following empirical polarizability scale: H 0.35; C 1.3; N 1.0; O 0.6; S 2.9; F 0.4; Cl 2.3; Br 3.2; I 5.0.

Based on this initial choice, extreme values were defined, for each variable, as shown in the table below (Step 4):

| Variable | Maximum | Minimum |
|---|---|---|
| M.W | 822 | 60 |
| FLEXI | 34 | 0 |
| SIZE | 14 | 1 |
| RIGID | 12 | 0 |
| QMINUS | 0 | −4 |
| QPLUS | 5 | 0 |
| HBACC | 14 | 0 |
| HBDON | 16 | 0 |
| LIPO | 10 | −10 |
| POLAR | 120 | 5.2 |

Having defined extreme values for the above variables, a number of 61 existing or hypothetical compounds were assigned as satellite objects (Step 5). thus, an initial set of 189 objects with 10 calculated variable datapoints was defined (step 6). This was the initial set of rules.

The set of rules chosen in step 6 was not refined (step 7).

The dataset described in steps 6 and 7 was subjected to PCA, rendering an initial model with three significant (by cross-validation) principal components (Step 8).

The 45 aromatic structures described by Clementi et al. [1] were predicted (step 9).

We did not find any outliers (STEP 10a). However, a better description of the property space was required (Step 10b).

Therefore, the descriptor set was refined (step 11b), and included 62 descriptors in the final analysis (before Step 12 was performed). Among these descriptors, some were topological indices, some were related to electrostatic properties, and some were related to hydrogen bond acidity/basicity. All descriptors were calculated using commercially available software.

At this stage, the model included 189 structures, out of which only 61 were satellites. The internal structure of our dataset was considered imbalanced. Therefore, a set of 48 additional satellites were included (step 12).

The model was redefined using PCA, for a set of 237 compounds and 62 descriptors, providing eight significant principal components (Step 13).

This model was found satisfactory (Step 14), as no structures were outliers according to outlier detection methods, e.g. DmodX (distance to Model X) and PCA score distribution.

Variable score values for the 45 aromatic structures were predicted by the model produced in step 13 (step 15).

No outliers were observed in the external dataset (Step 16).

Therefore, final score plots were produced for the first four principal components. These were used for navigation in chemical space. For the purpose of illustration, we compared our score plots to those produced by Clementi et al.

We found that we could position those heterocyclic compounds in an appropriate part of the chemical space (FIG. 2) and also see informative distribution on the local level (FIG. 1) that compares to the score plot based on original data by Clementi et al. (FIG. 3).

Figure 2:
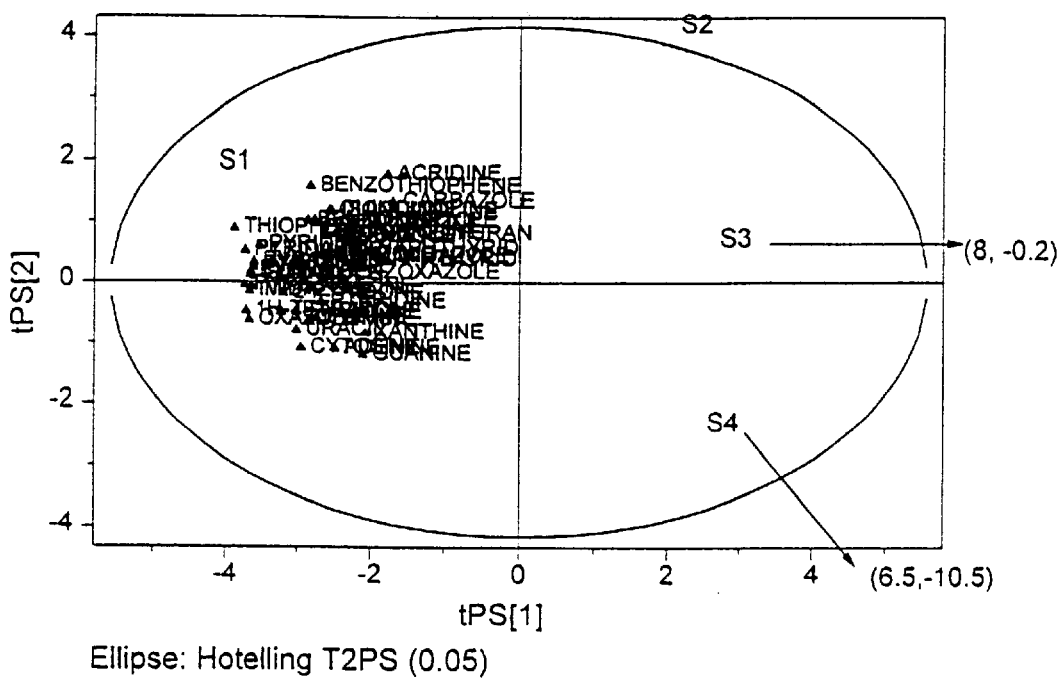

FIG. 2 shows the positioning of the heterocyclic compounds described by Clementi et al, using the suggested global model system. Some satellites are indicated, i.e. S1–S4. Note that S3 and S4 are positioned out of the scale (co-ordinates for abscissa and ordinate as indicated in parentheses). S1, Carbon tetra-chloride; S2, Tetraphenyladamate; S3, Vinblastine; S4, Tetra-Arginine.

FIG. 1 shows a close-up on FIG. 2 for investigation of local resolution using the present system.

Figure 3:
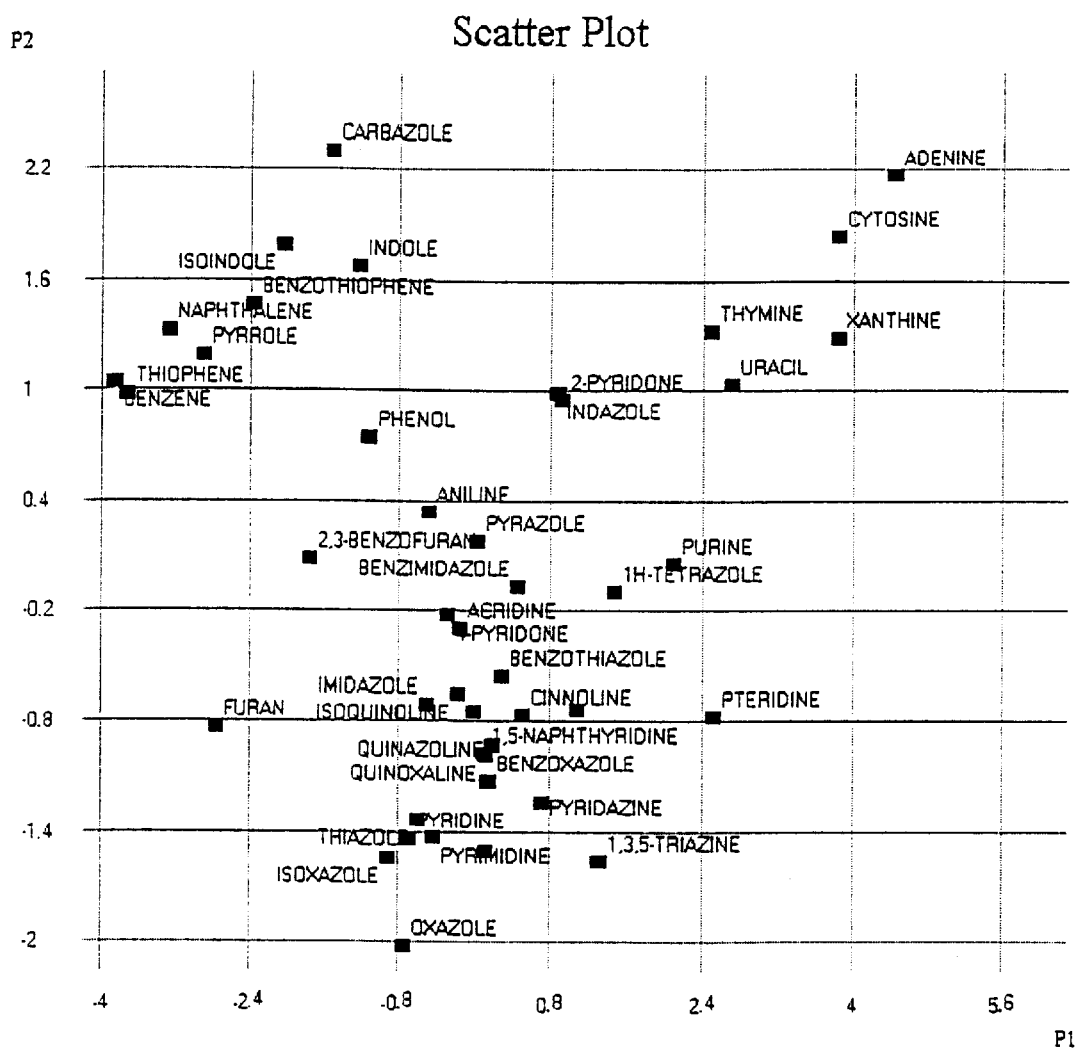
FIG. 3 is an example of a local map.

FIG. 3 shows the positioning of 45 heterocyclic compounds by the approach used by Clementi et al, reproduced by us.

As seen in FIG. 2 the included heterocyclic compounds are positioned close to carbon tetra chloride (satellite S1) in the global chemical space.

The results show that the global model produced using the technique described herein is consistent with the previous local model and yet has much more general applicability.

Extreme values may be defined as discussed above in relation to Step 4. A more broadly based model may be produced, if desired, using the following alternative extreme values.

| Variable | Maximum | Minimum |
|---|---|---|
| M.W. | 1500 | 30 |
| FLEXI | 50 | 0 |
| SIZE | 50 | 0 |
| RIGID | 30 | 0 |
| HB ACC | 35 | 0 |
| HB DON | 25 | 0 |
| POLAR | 150 | 0 |

As an alternative to determining the SIZE value as discussed above, a measure of this may be made by determining the "calculated molecular refractivity, CMR", such as by the Daylight CIS software. In this case suitable extreme values are 35 and 0. A further alternative would be to calculate the molecular volume (MVOL) of a molecule by summing the consituent atomic volumes derived using the van der Waals radius of each atom. In this case suitable extreme values would be 2000 and 20 cubic angstoms.

Figure 7:
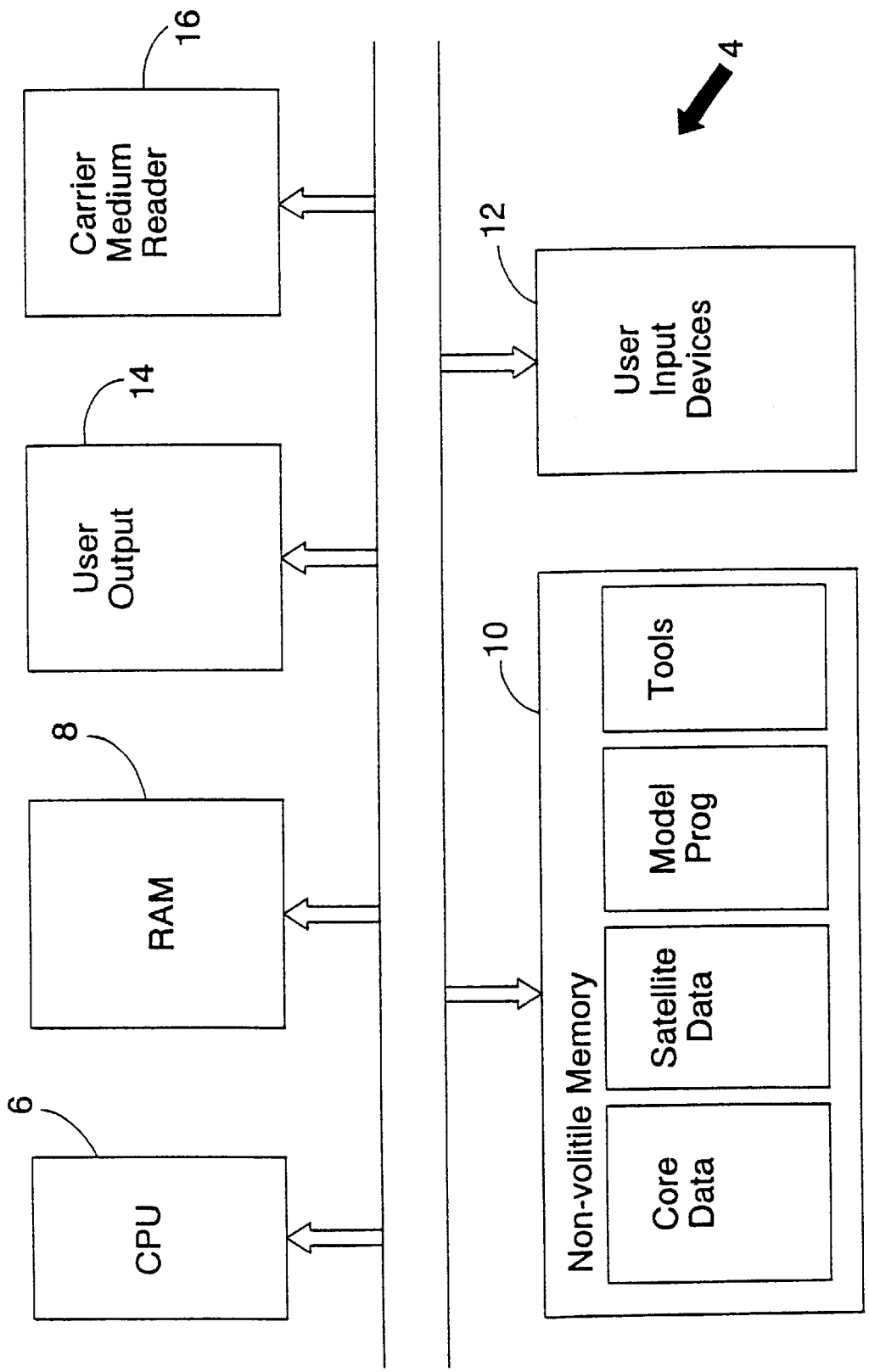
FIG. 7 schematically illustrates a computer for performing modelling.

FIG. 7 schematically illustrates a computer system of the type that may be used to implement the modelling technique described above. In general terms, the computer system 4 contains a central processing unit 6, a working memory 8, a non-volotile memory 10 (such as a hard disc drive), a user input device 12 (such as a keyboard and mouse), a user output device 14 (such as a computer monitor or printer) and a carrier medium reader 16 (such as a CD Rom drive, floppy disc drive or telecommunications connection). The central processing unit 6 executes program instructions loaded from the non-volatile memory 10 into the working memory 8. These program instructions define the processing steps for performing the modelling technique described above. The non-volatile memory 10 will also include programs for running the various tools for determining properties of the target compounds of the type discussed previously. Also stored within the non-volatile memory 10 is the core object data and the satellite object data that serve to form the N-dimensional model.

A user of the computer system 4 will manipulate the user input device 12 to initiate the running of the modelling program and will input parameters describing the target object to be modelled. In a typical example a library of target objects of potential interest for screening may be input to the model such that their similarities and differences to existing known pharmaceuticals can be studied before a decision as to whether or not to screen those compounds for biological activity is made. When the target objects have been positioned within the model incorporating the core objects and the satellite objects as described above, a user output may be generated using the user output device 14 to display the relative positions of the target objects within the target hyper-volume. The displays may typically be projections into various 2-dimensional planes from the N-dimensional model.

The computer program that performs the model will typically be formed of control instructions together with the associated core data and satellite data. These items may be loaded into the non-volatile memory via the carrier medium reader 16. A commercial product embodying the model of the invention may comprise a carrier medium sold for use by a user having first loaded that carrier medium into their computer system 4 via the carrier medium reader 16.

FIG. 8 schematically illustrates a comparison between the local model and the global model approach. Plot A represents a 1-dimensional local model containing four known objects signified by the solid dots. A target object to be positioned within that model is illustrated by the dashed circle. Providing that target object is of a generally similar type to the core objects within the 1-dimensional model, then a reasonable representation of its relationship to the other objects may be obtained by calculating its position within that 1-dimensional model.

It will be appreciated that a 1-dimensional model has been shown for ease of representation. In practice even a simple local model will typically include more than 3 dimensions and so be difficult to diagramatically illustrate.

Plot B illustrates the situation with a local model when one wishes to position within it a target object which is really too different from the other objects within the local model. In this case, a projection into the 1-dimensional model may be made, but this will tend to give an inaccurate representation of the similarity or differences of that target object from the other objects within that model. The local model does not properly span the property space and accordingly the projections made can result in misleading interpretations.

Plot C illustrates a 2-dimensional model following a global model approach. In this global model a target hyper-volume of interest 18 is formed within the 2-dimensional space and contains core objects illustrated by the solid dots. A number of satellite objects illustrated by crosses lie outside of the target hyper-volume. The inclusion of these satellite objects within the model has given the model a greater span of the property space. Accordingly, in this case when the target object is to be mapped into the target hyper-volume 18, a more representative relative position to the core objects is determined. This leads to a better understanding of the relationship between the target objects and the core objects and improves the general applicability and usefulness of the model.

A set of objects that can be used to form a model of chemical space is given in the attached Annex.

Core and Satellite objects

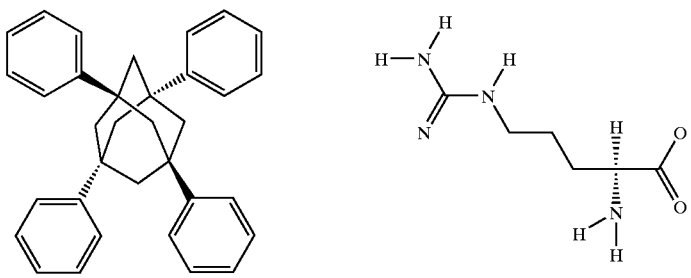

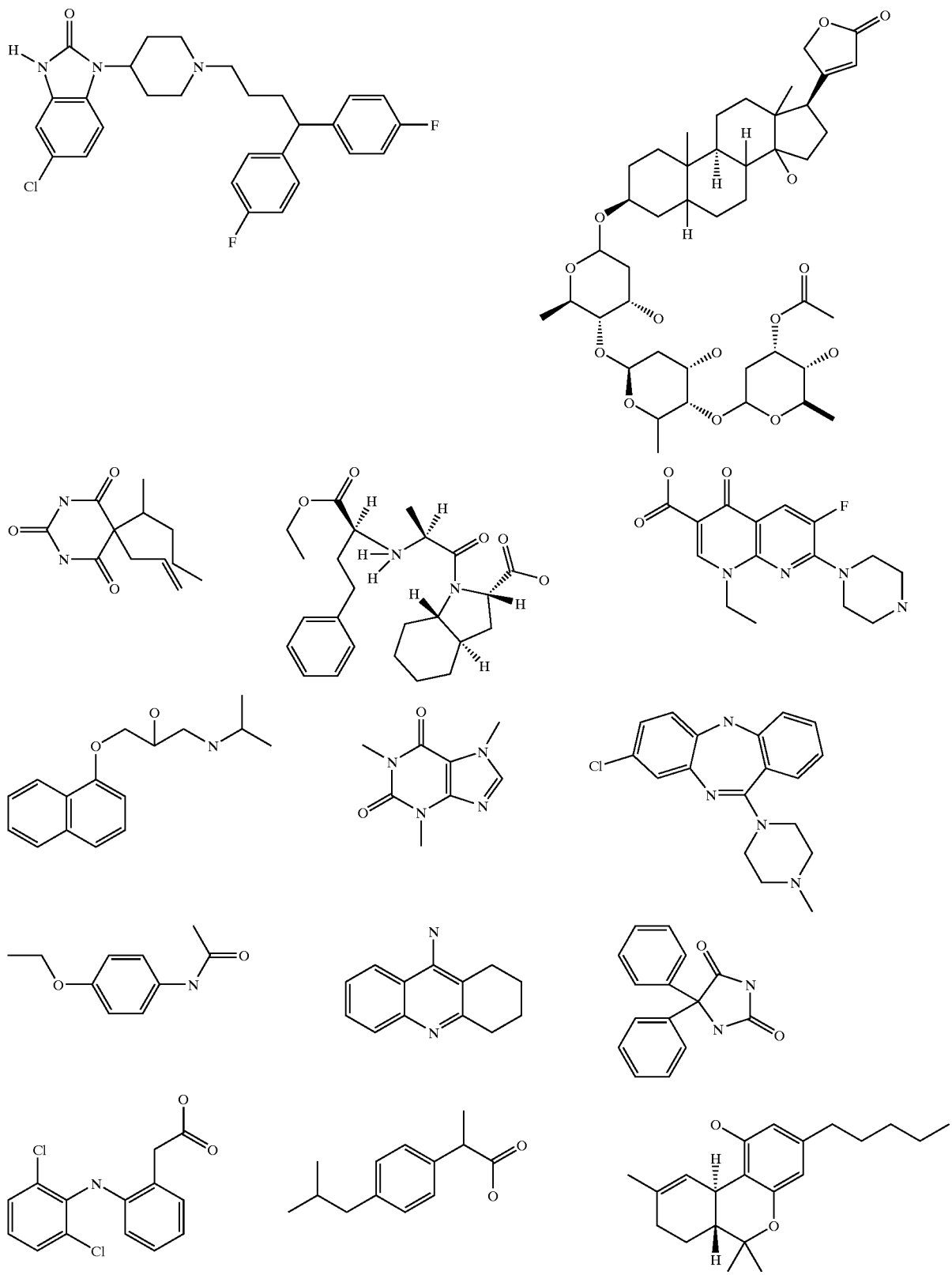

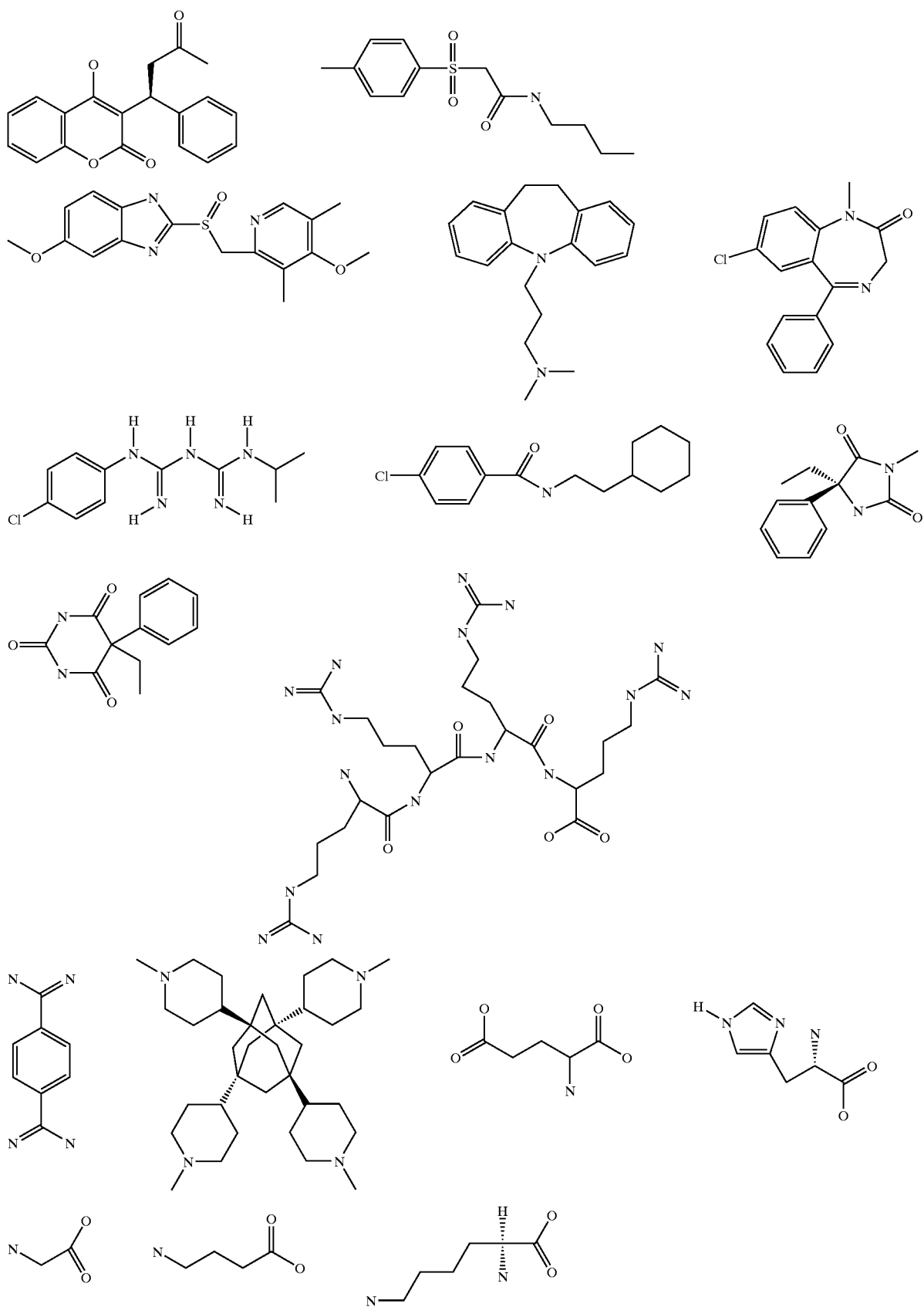

-continued
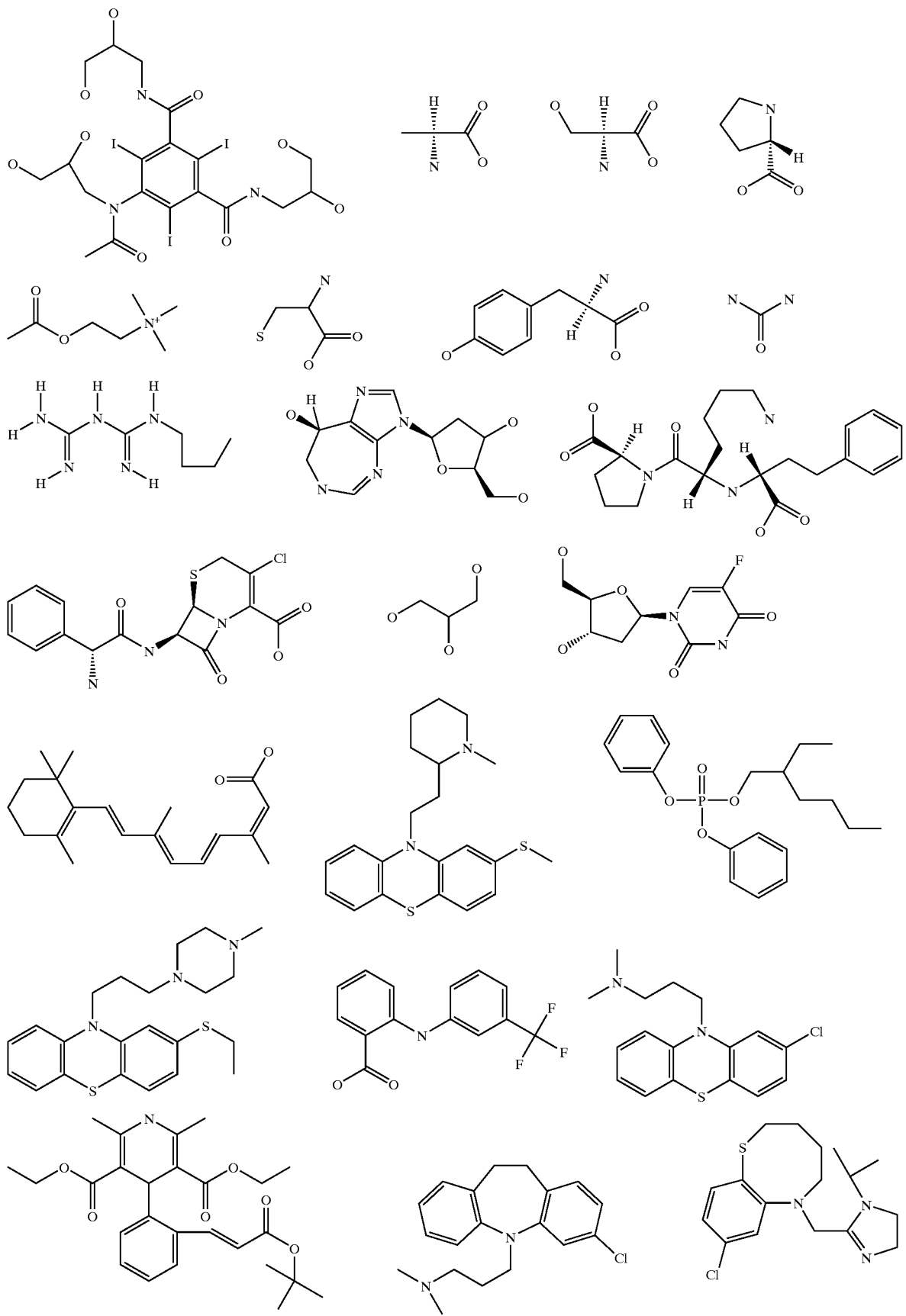

-continued
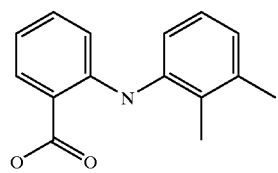
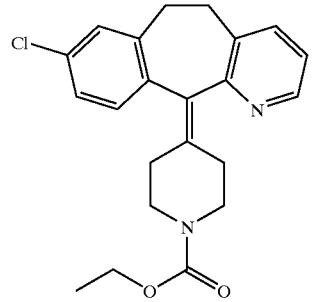
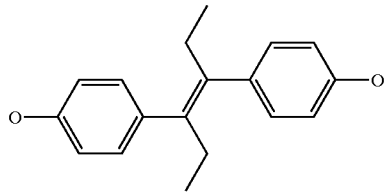
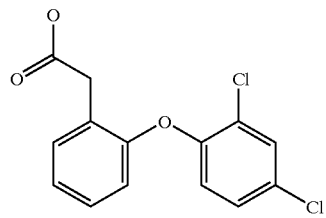
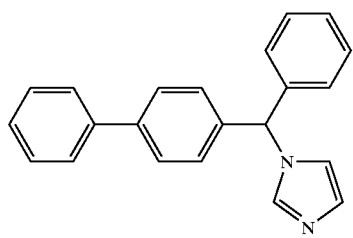
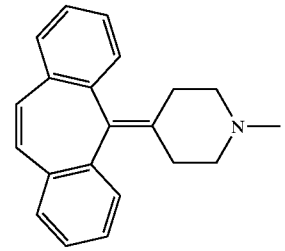
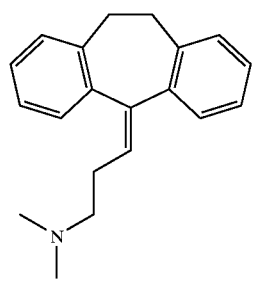
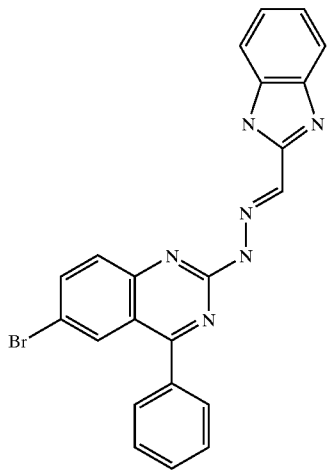
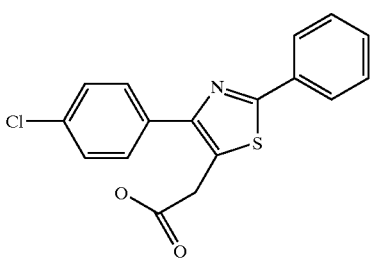
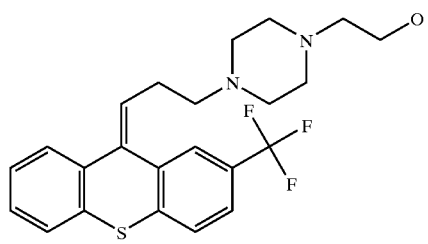
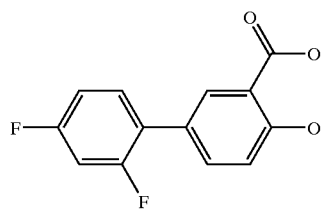
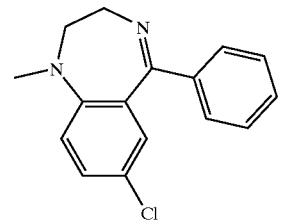
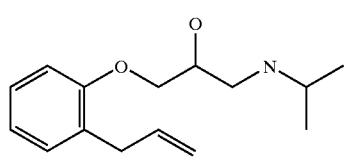
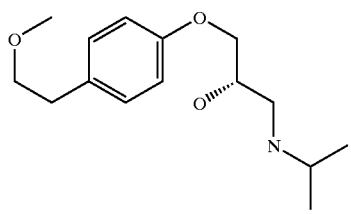
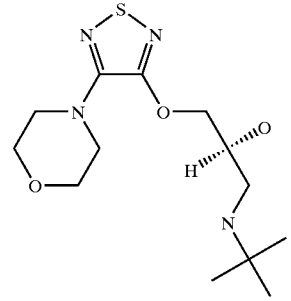

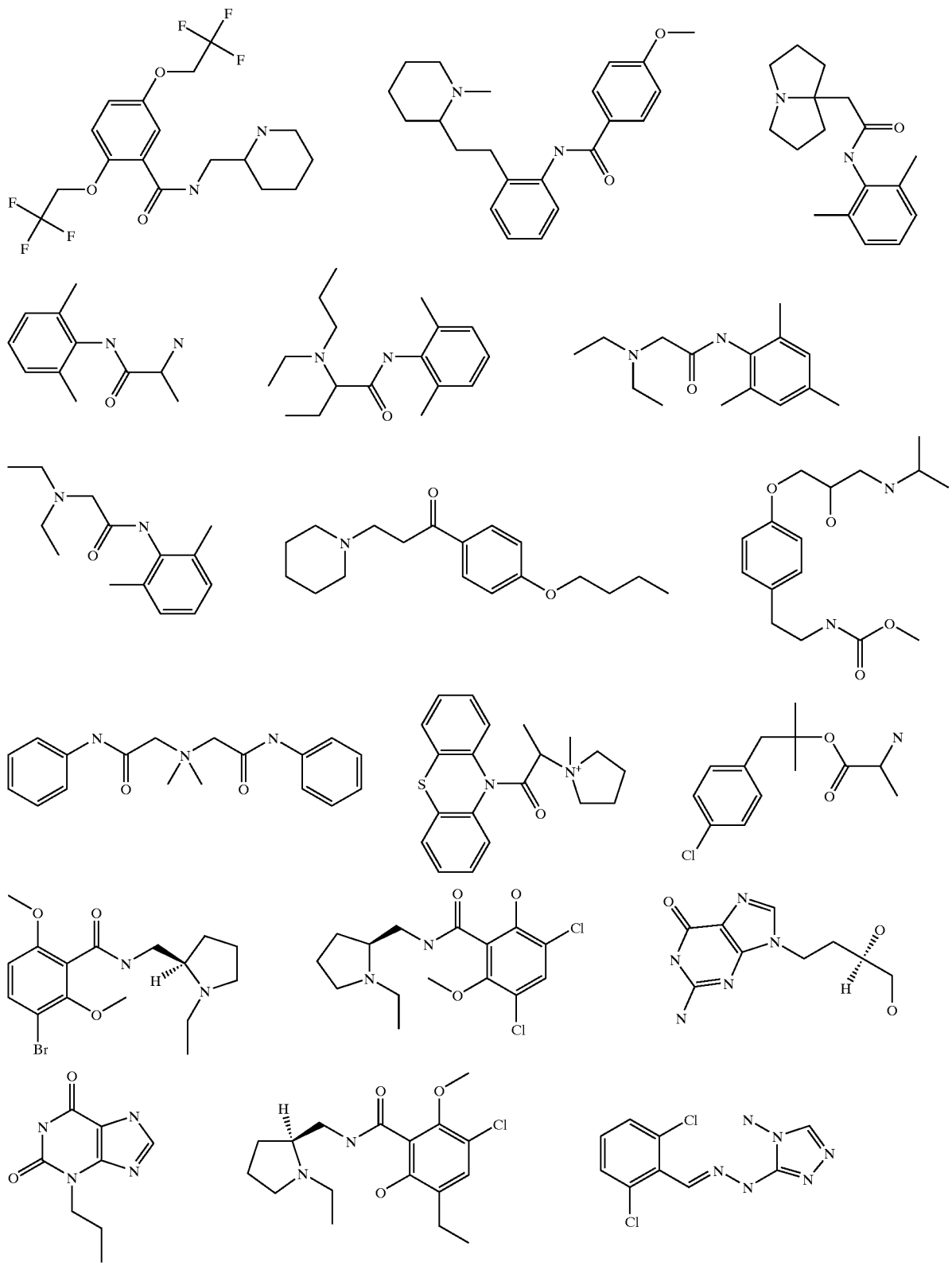

-continued
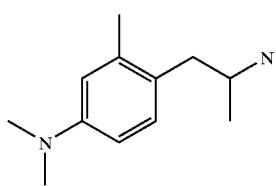
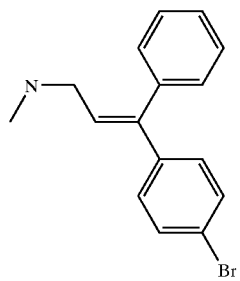
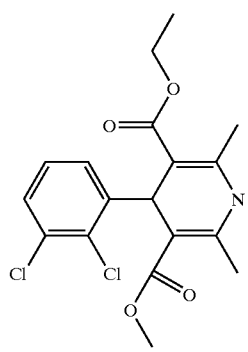
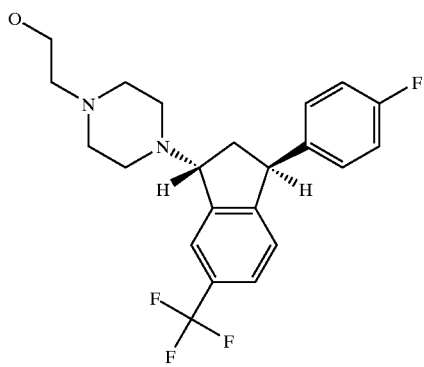
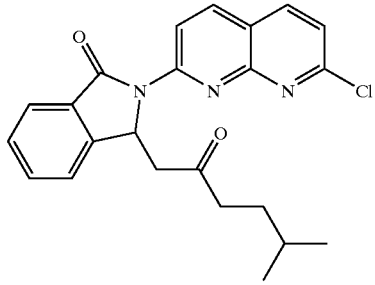
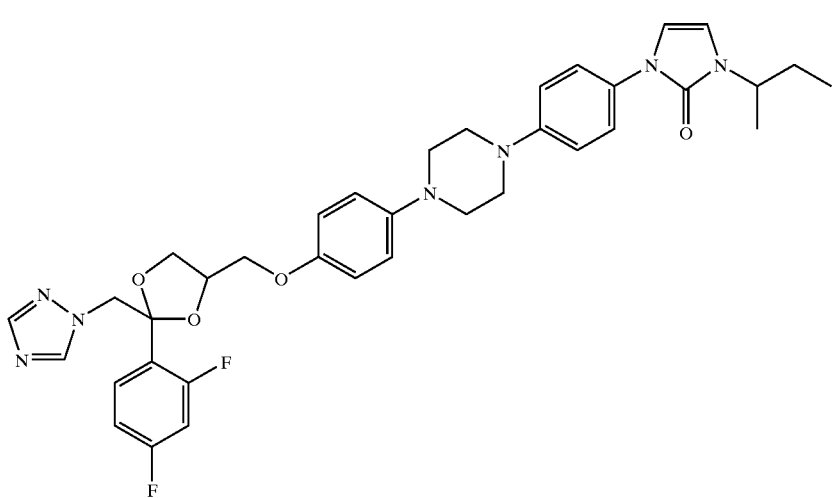
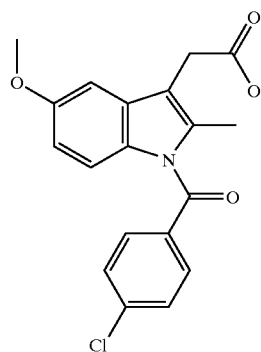
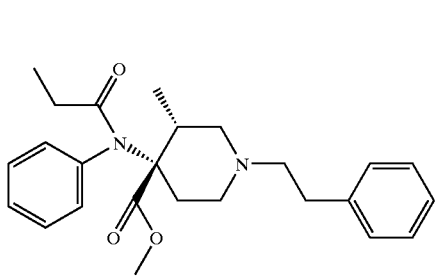
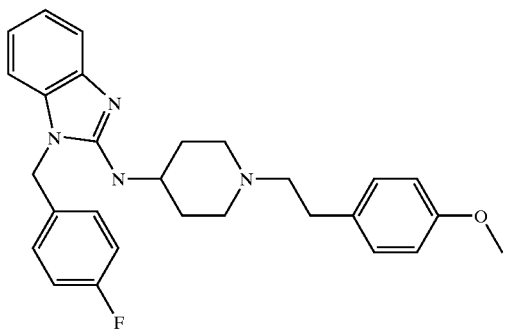

31
32
-continued
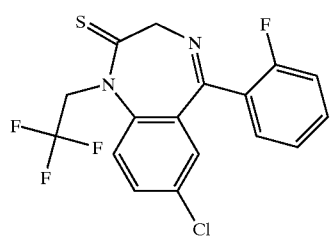 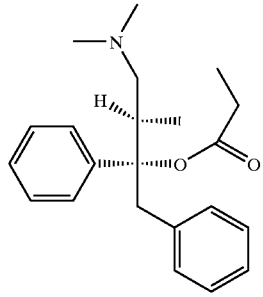 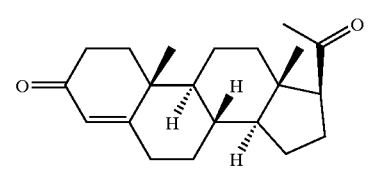
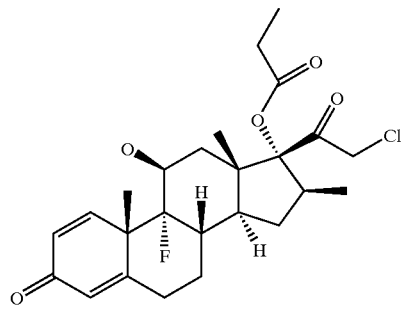 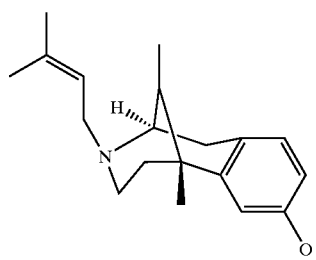 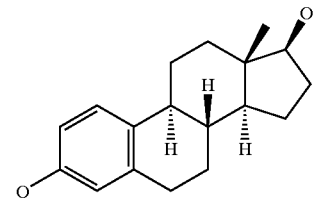
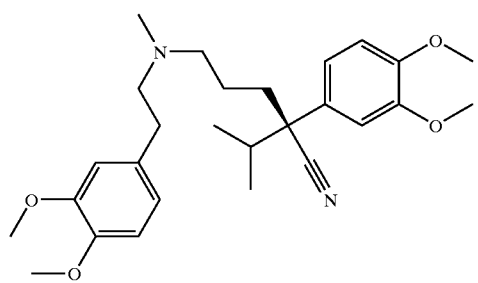 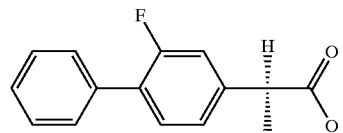
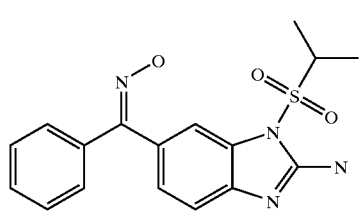 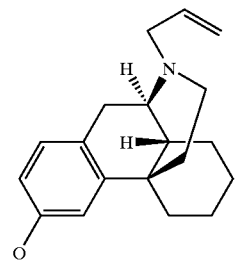 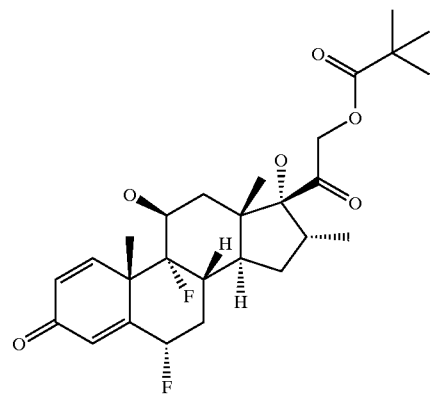
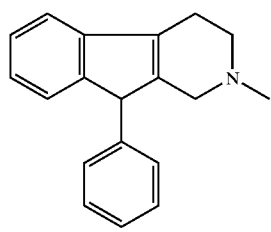 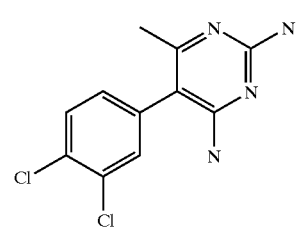 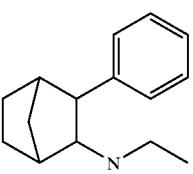 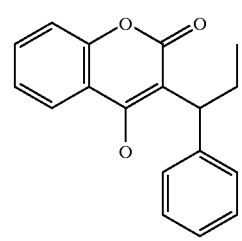

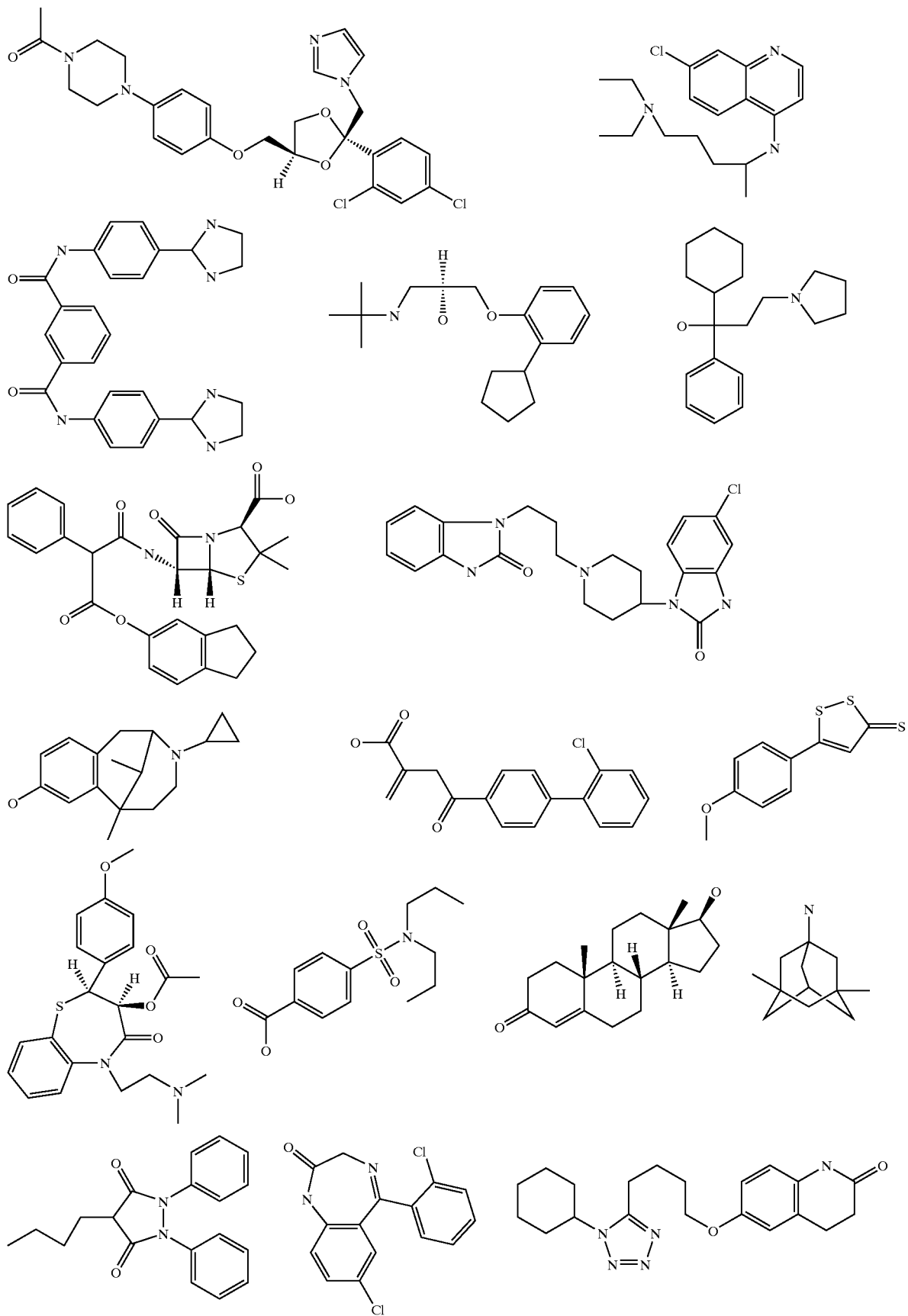

-continued
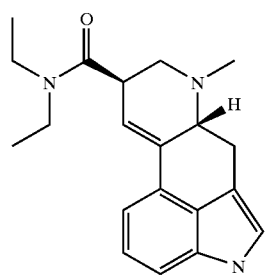
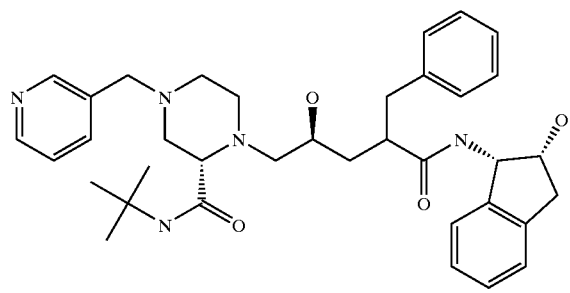
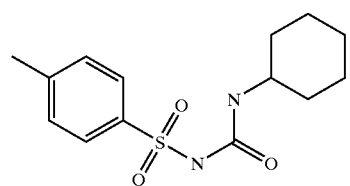
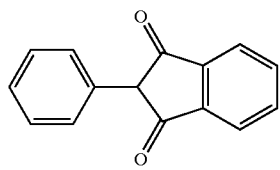
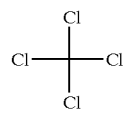
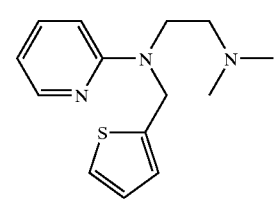
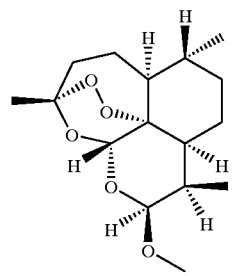
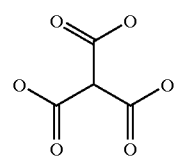
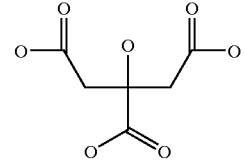
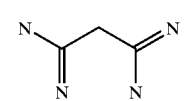
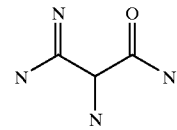
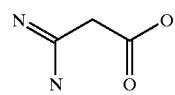
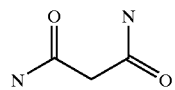
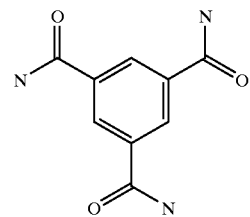
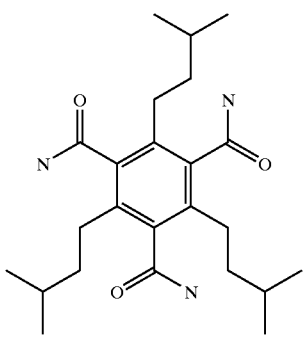
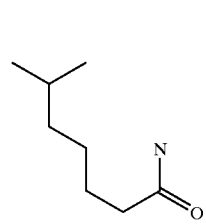
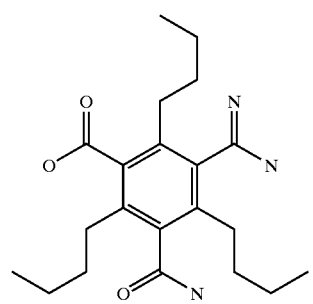
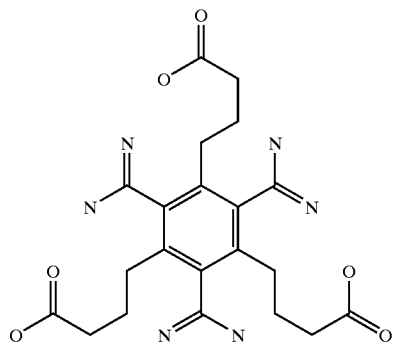

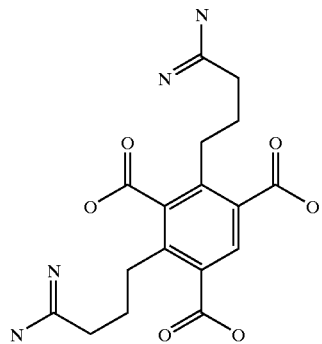
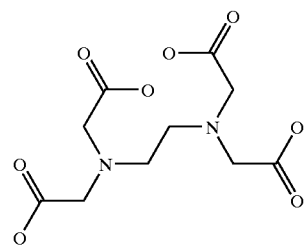
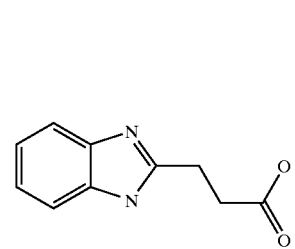
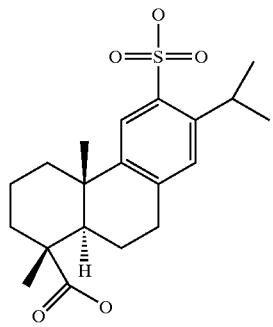
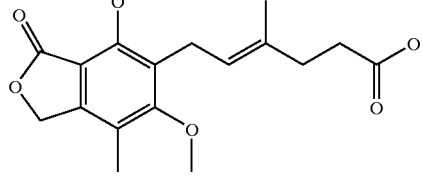
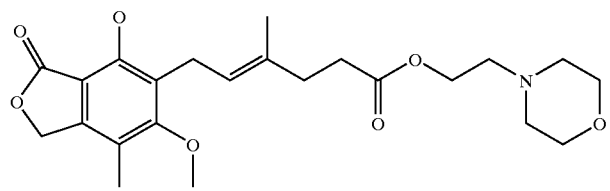
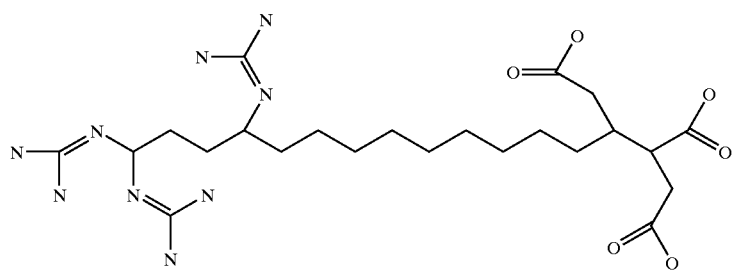
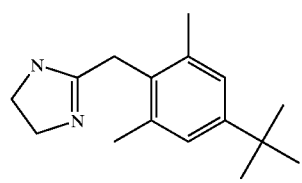
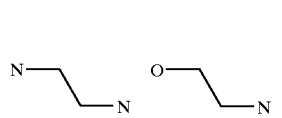
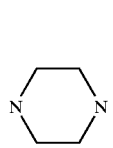
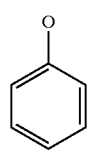
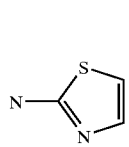
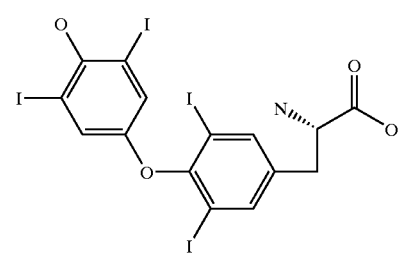

-continued
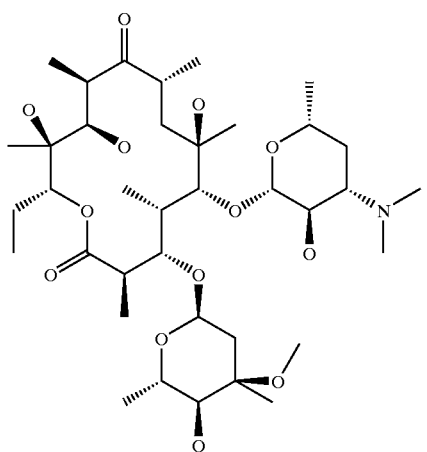
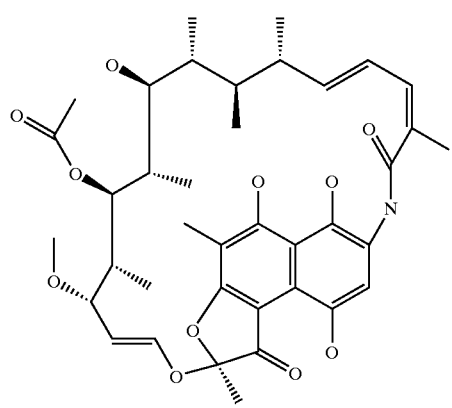
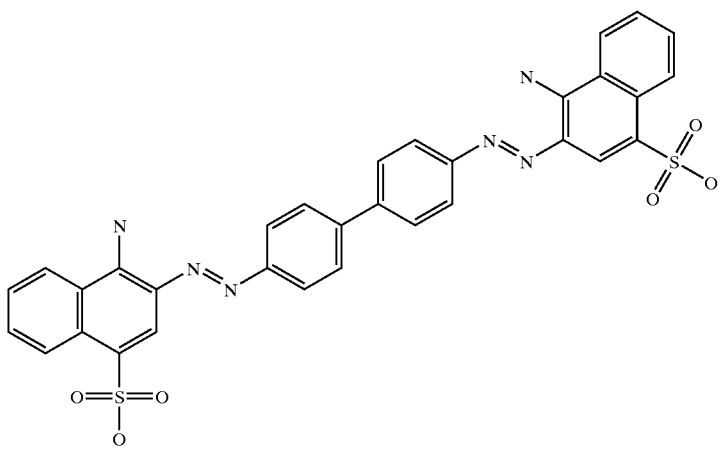
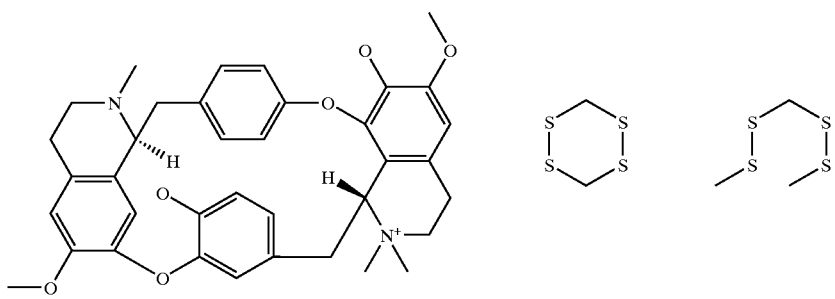
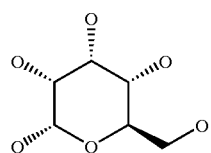
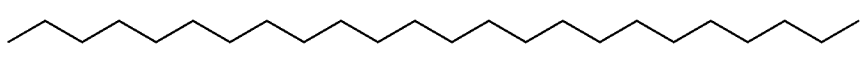
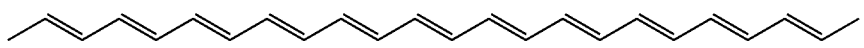
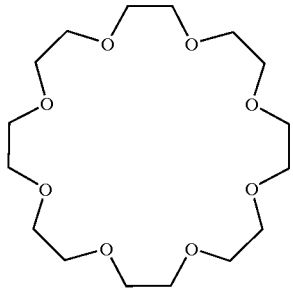
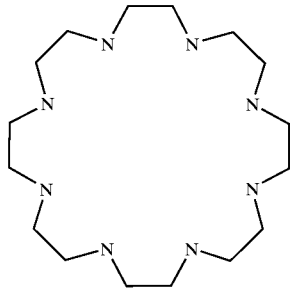

-continued
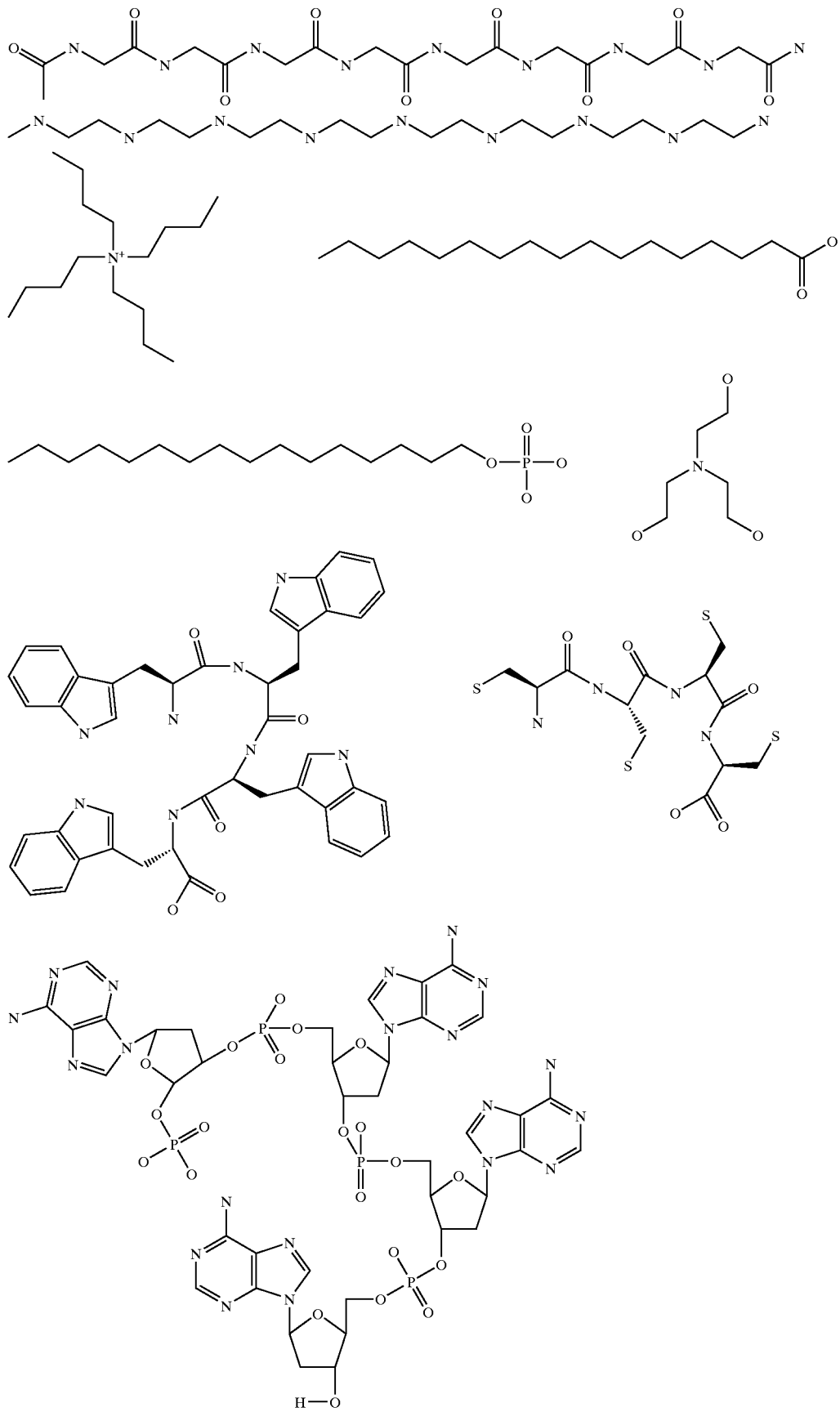

43
44
-continued
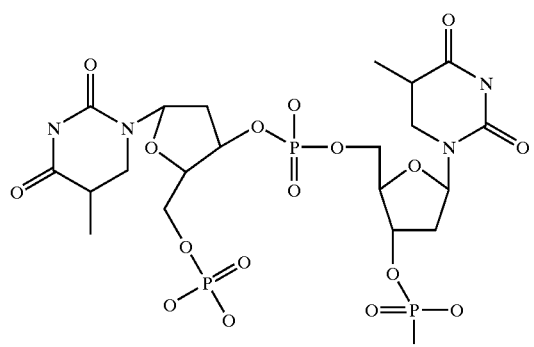
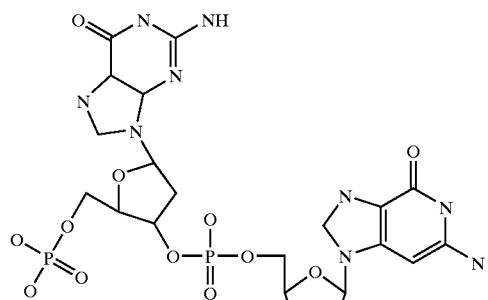
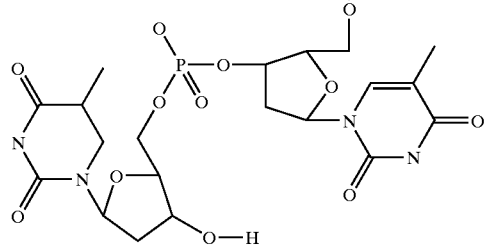
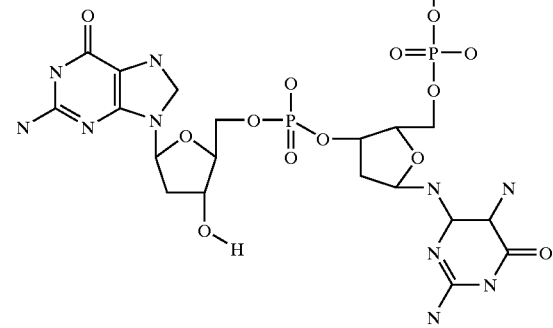
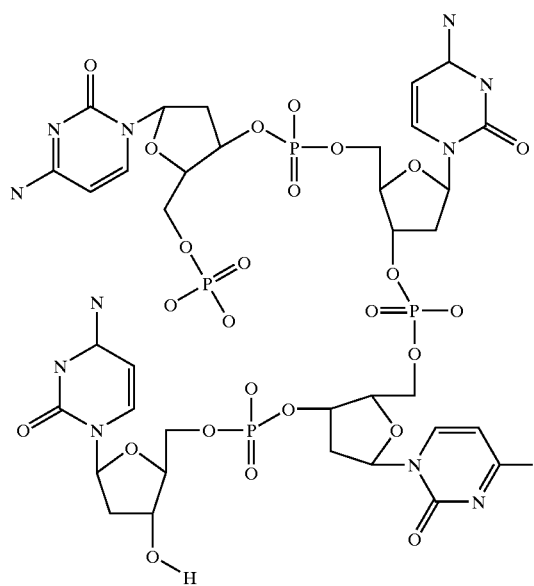
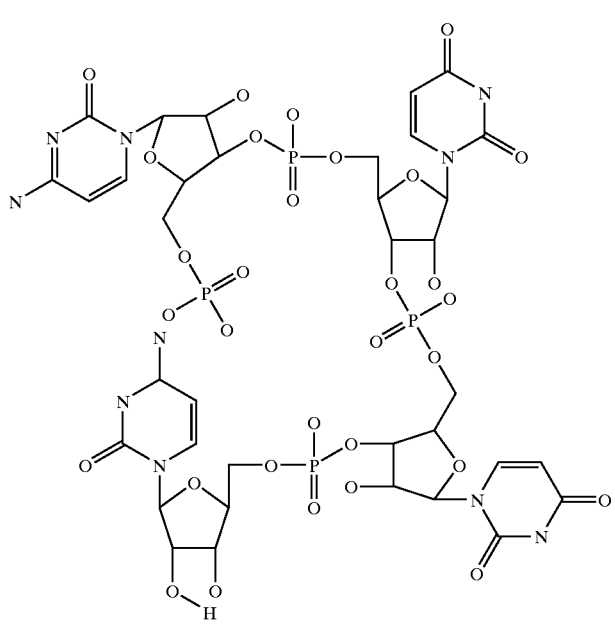
  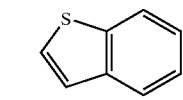     
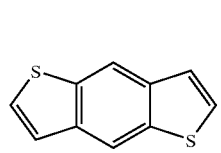 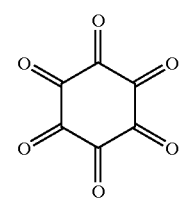 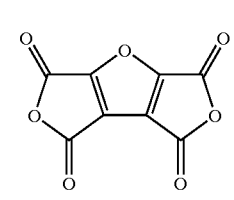 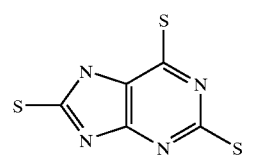 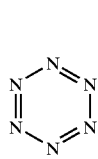

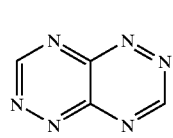
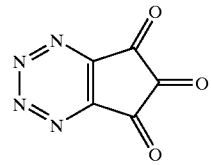
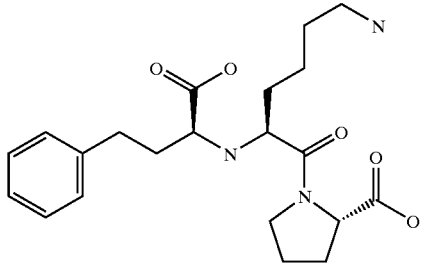
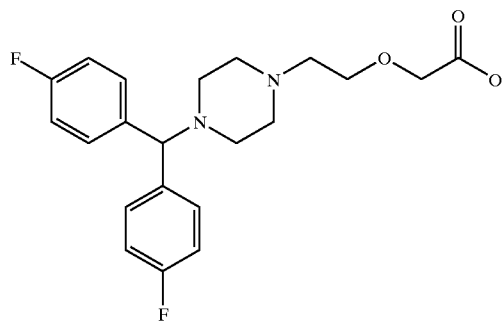
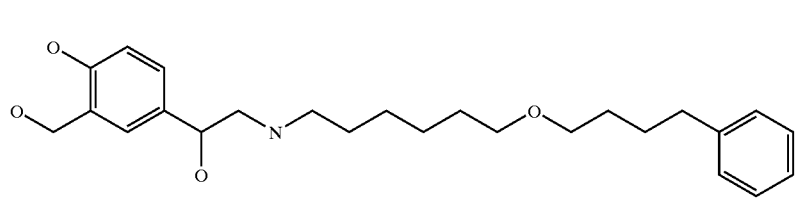
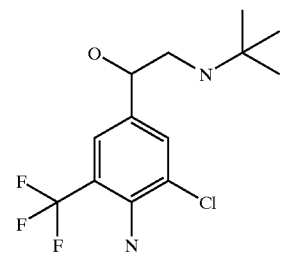
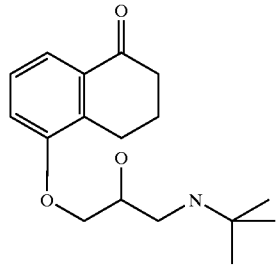
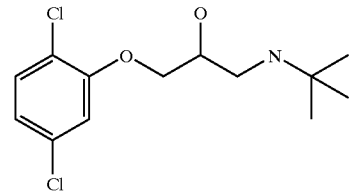
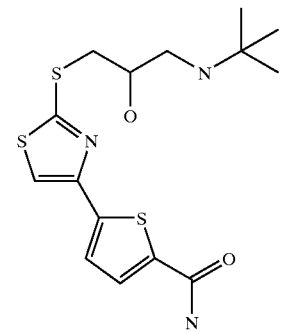
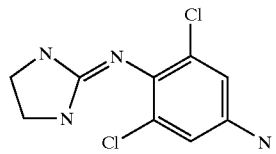
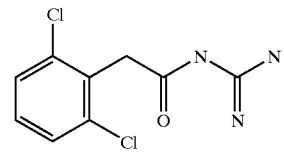
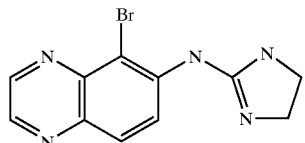
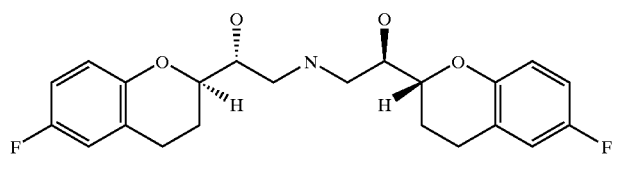
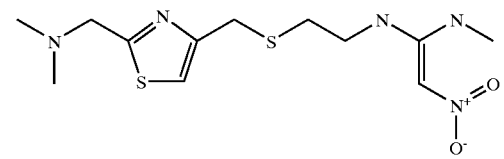
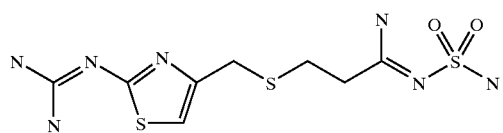
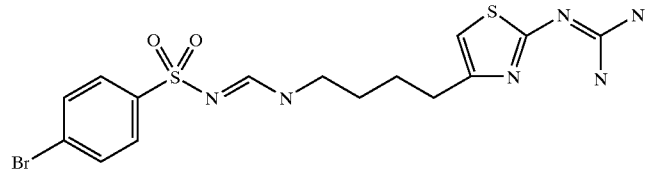

-continued
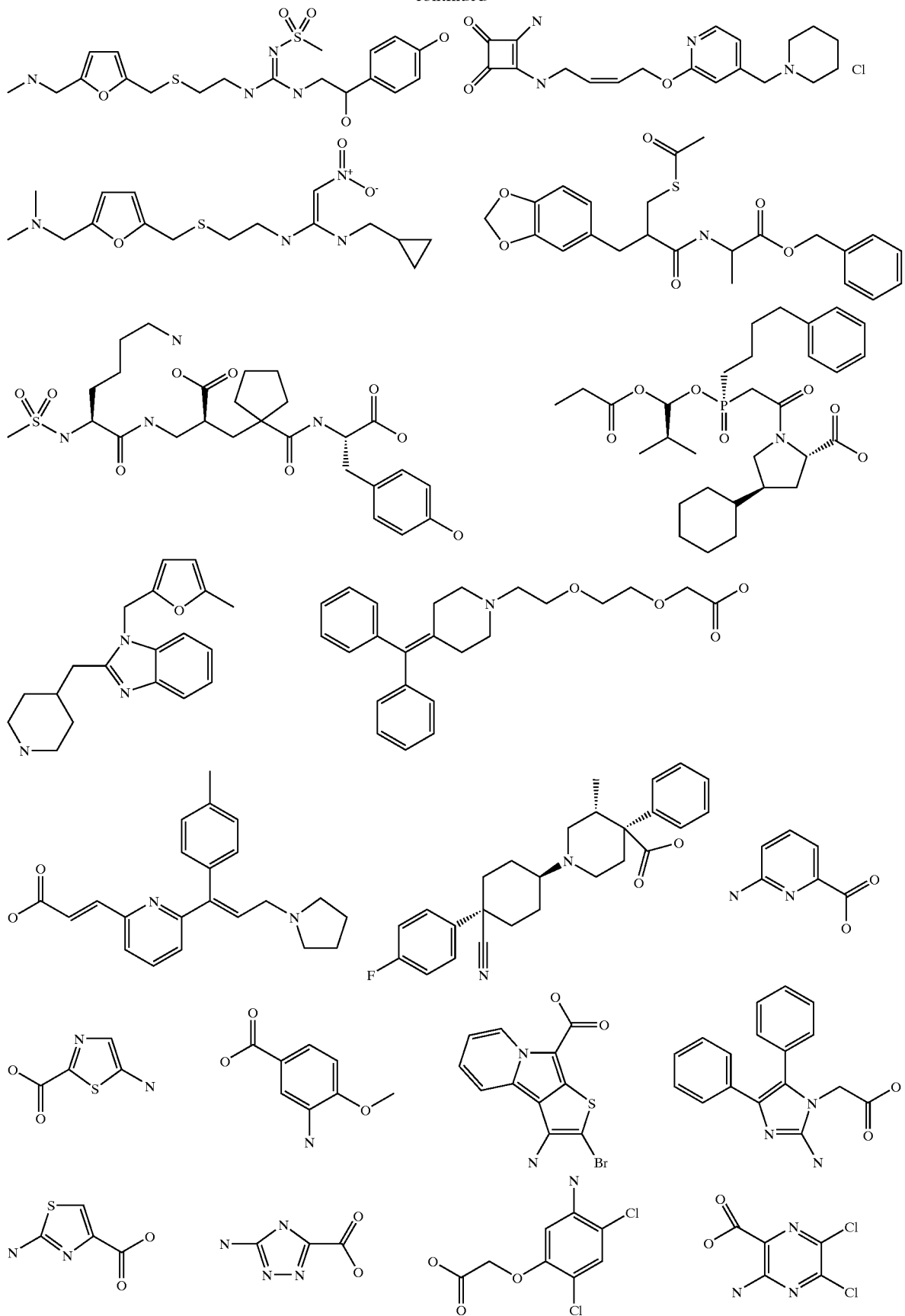

-continued
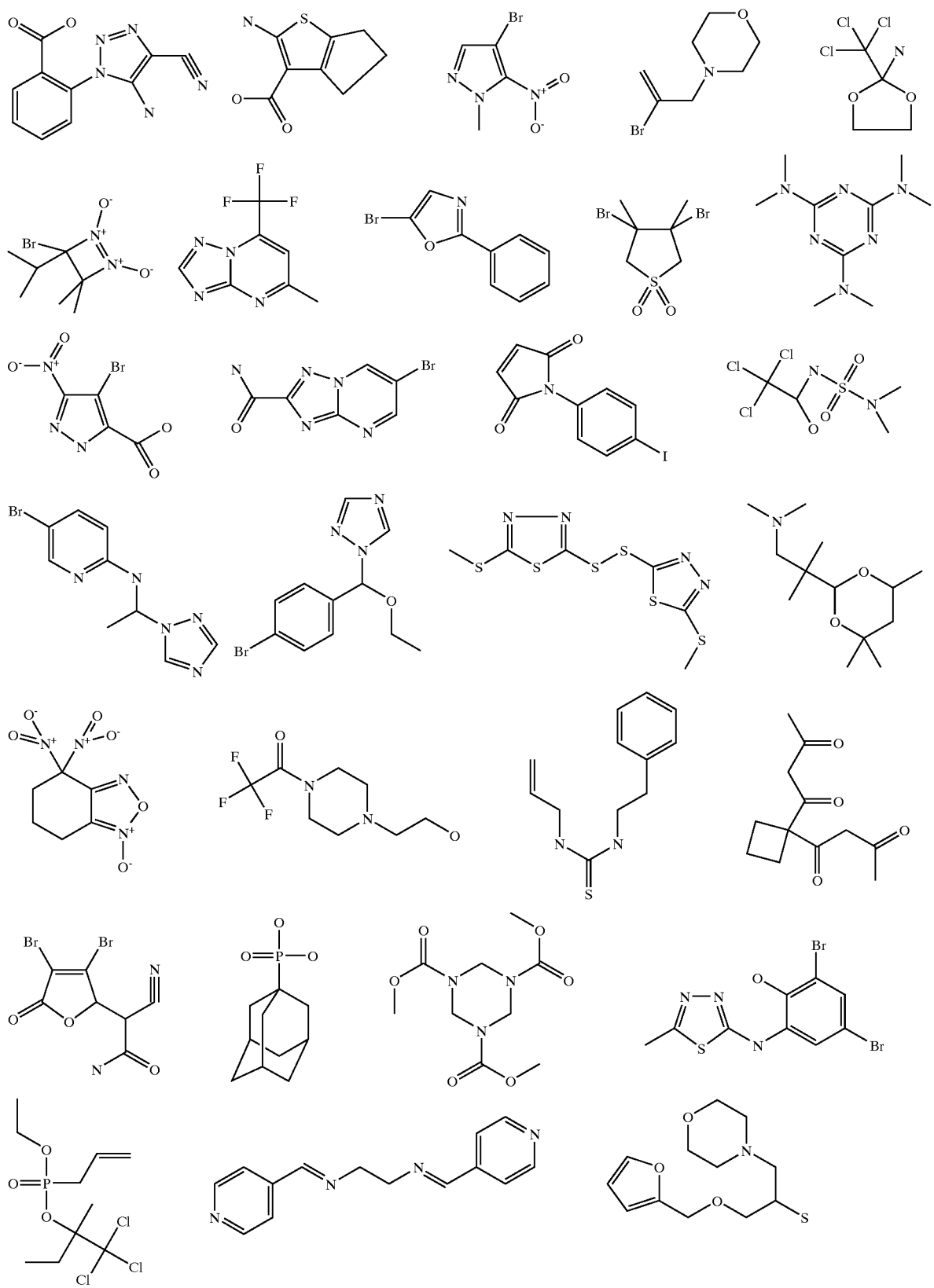

51  52
-continued
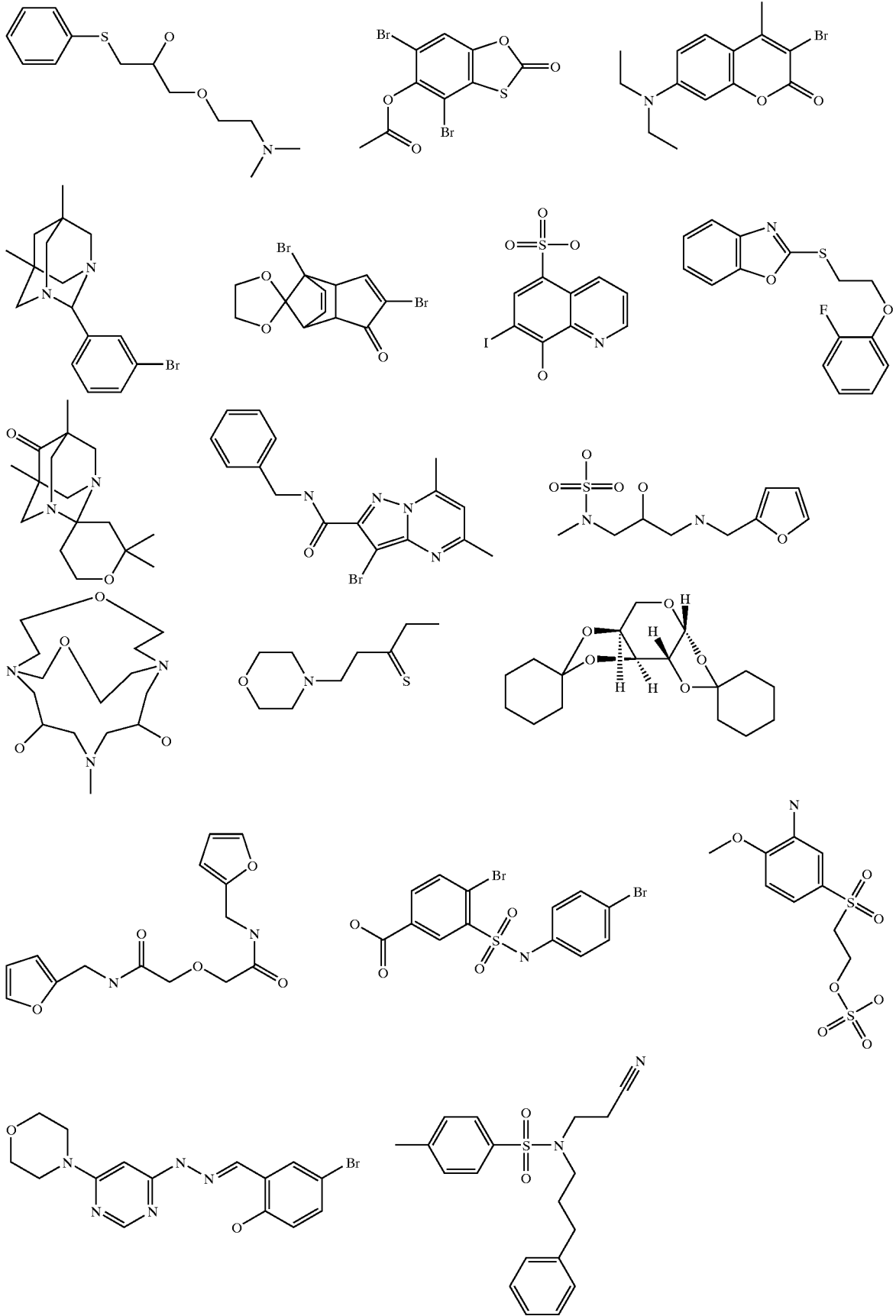

-continued
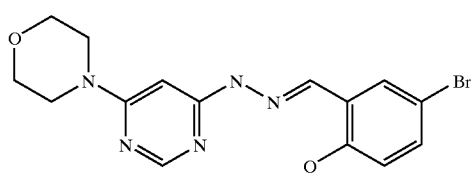
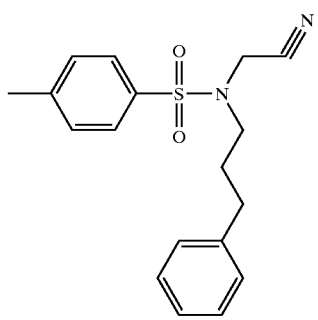
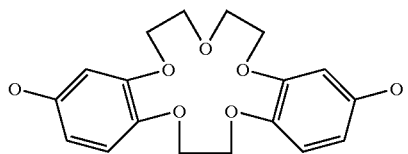
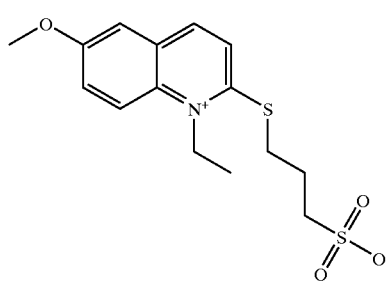
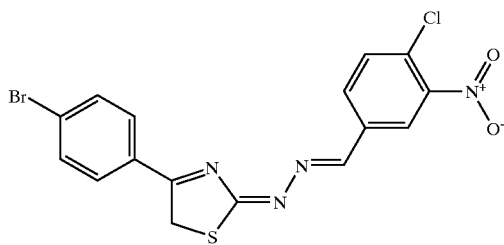
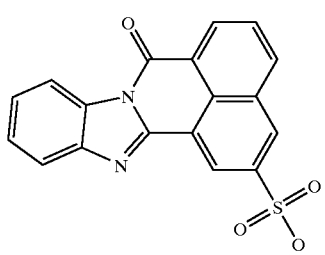
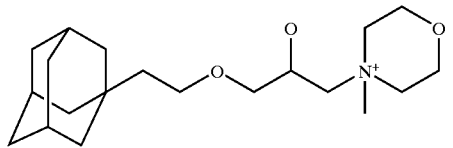
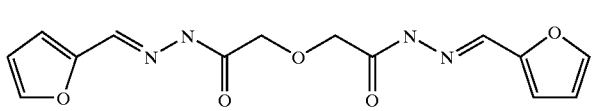
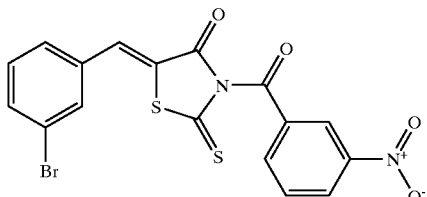
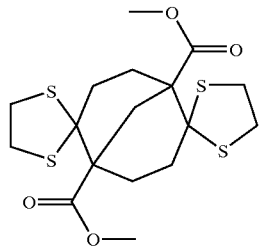
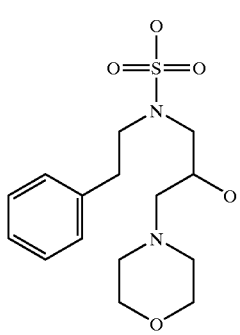
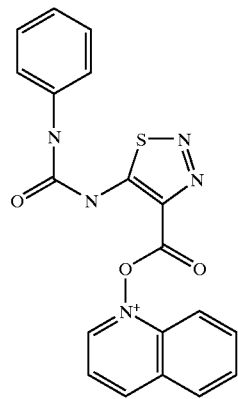
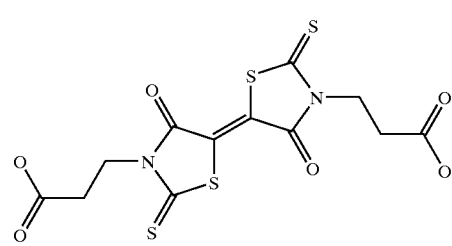

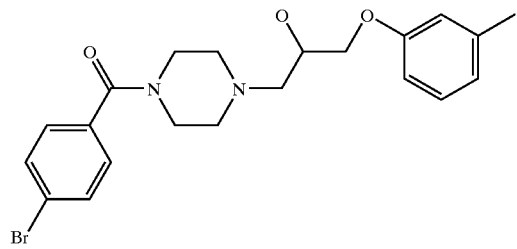
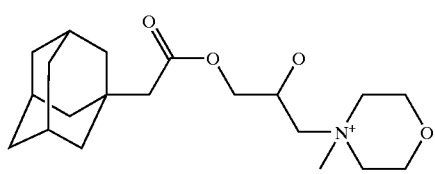
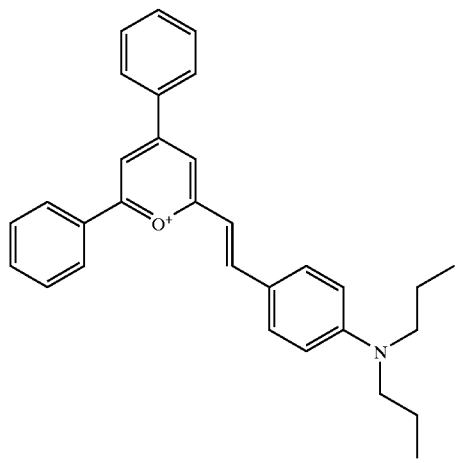
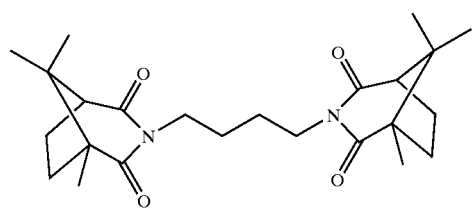
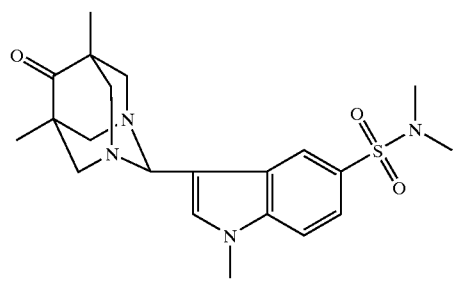
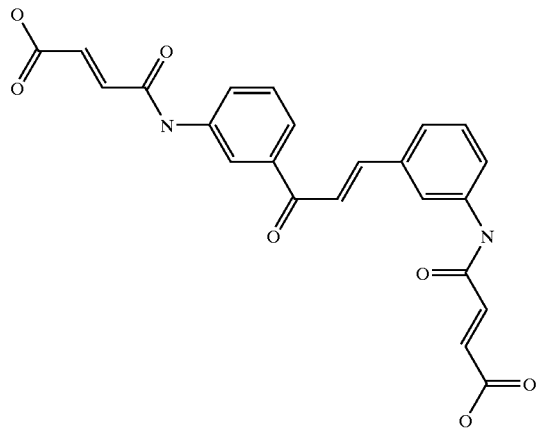
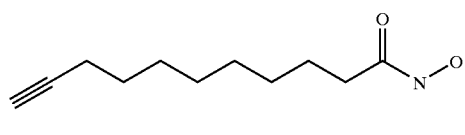
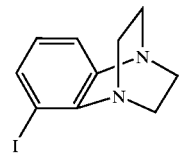
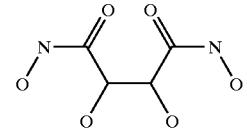
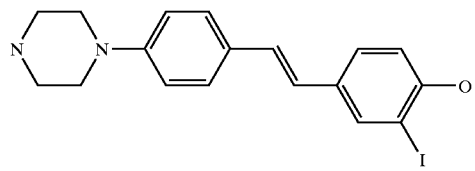
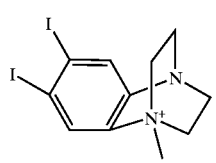
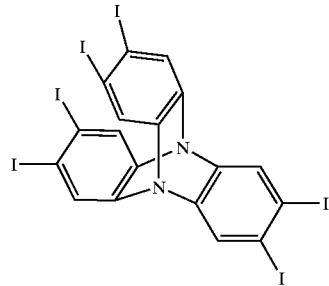

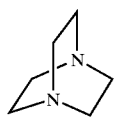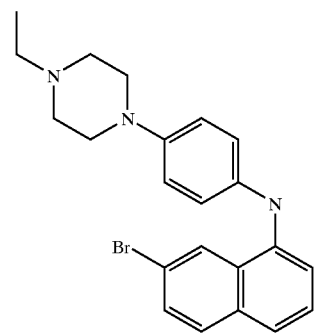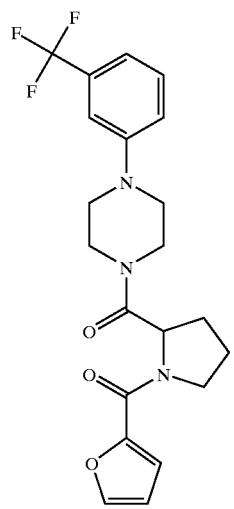
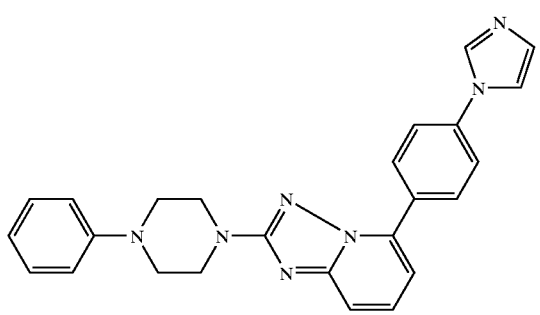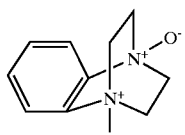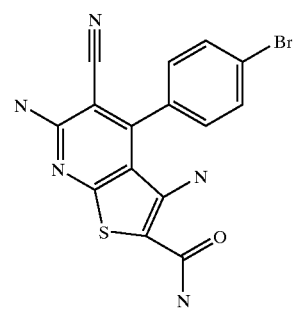
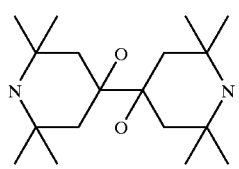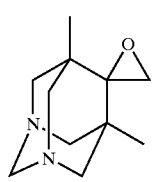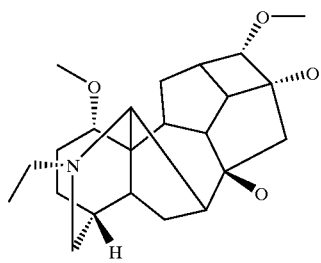
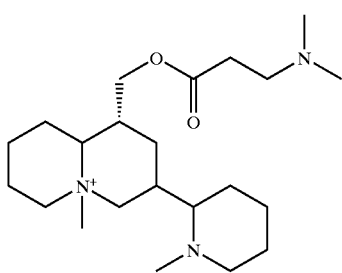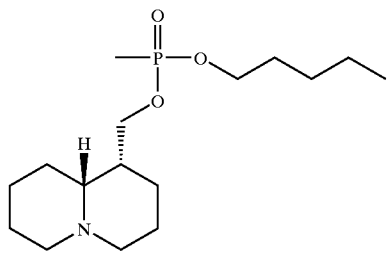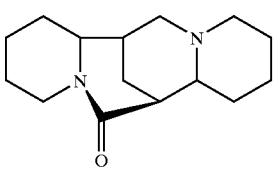
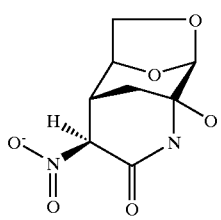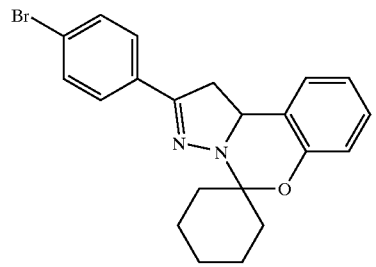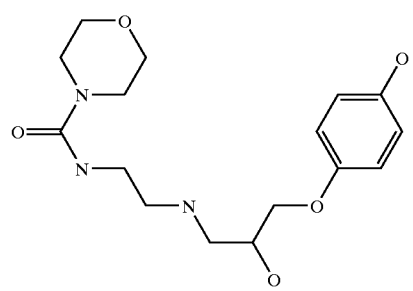

-continued
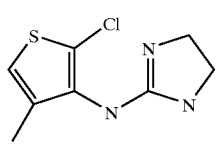
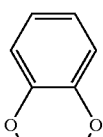
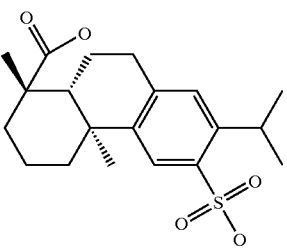
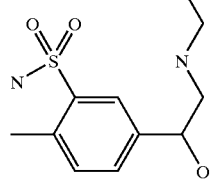
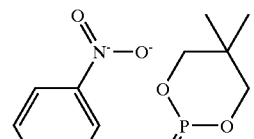
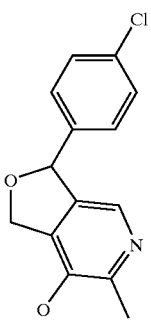
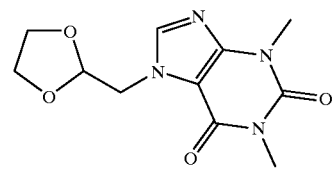
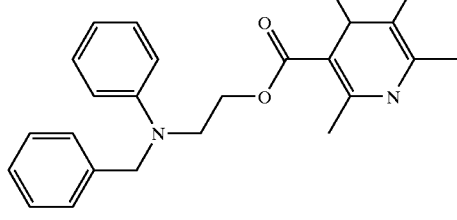
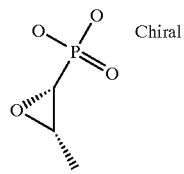
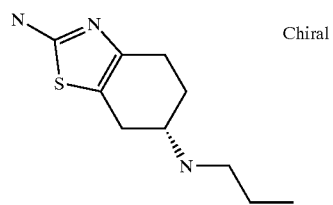
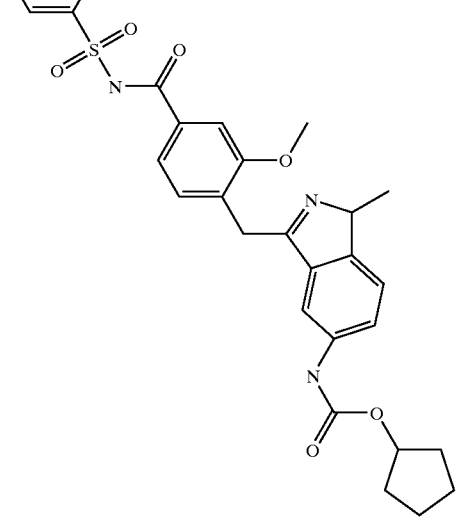
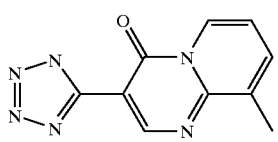
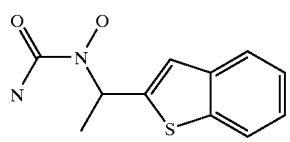
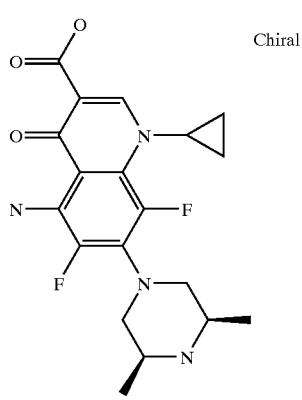

-continued
Chiral
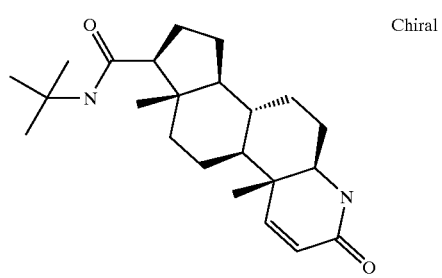 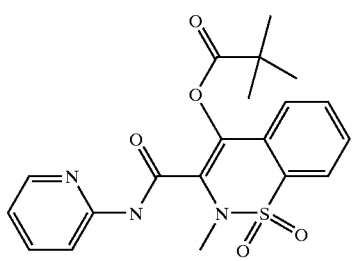 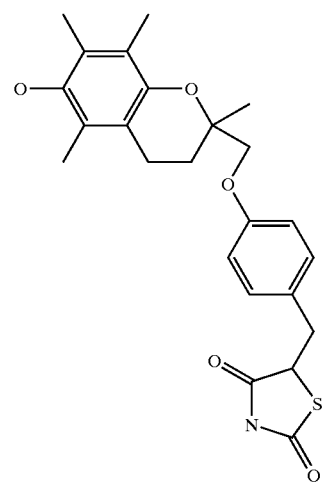
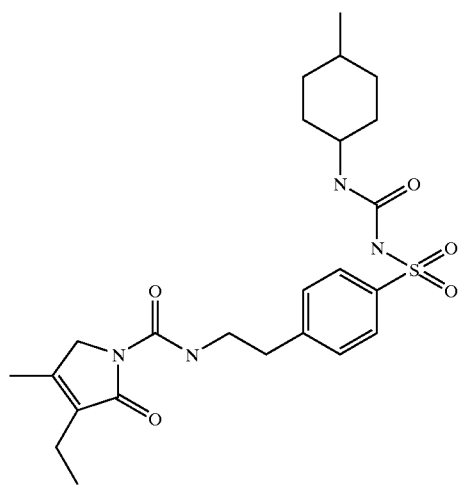 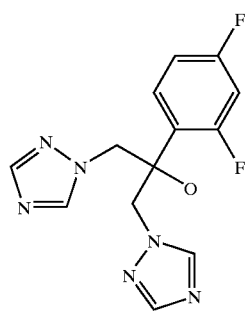 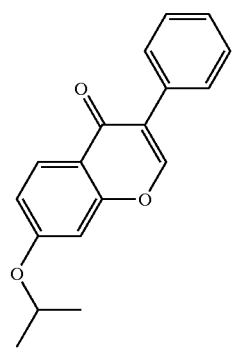
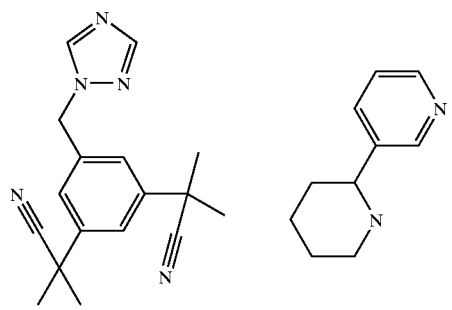 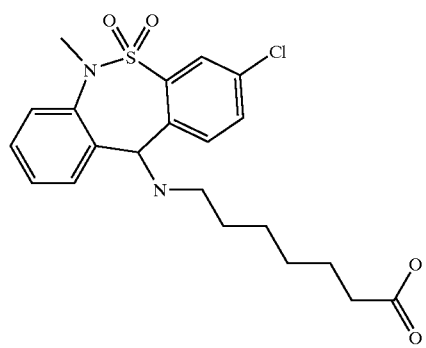 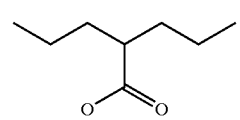
Chiral
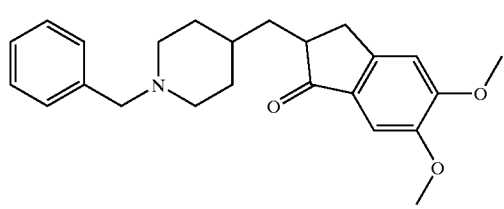 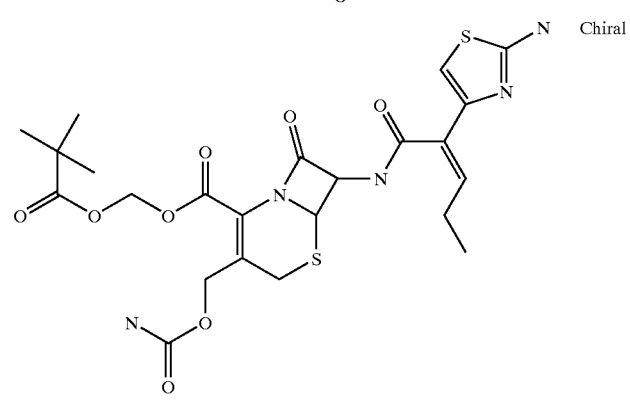

-continued
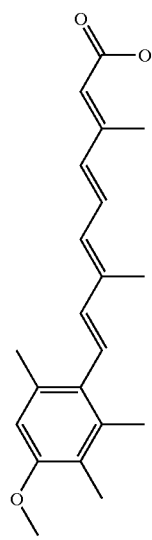
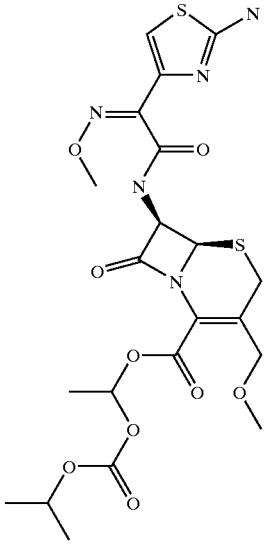
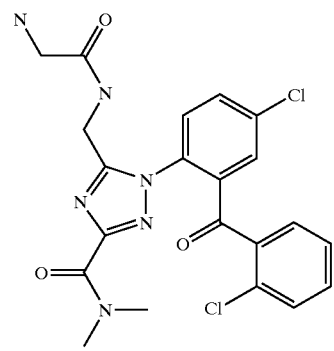
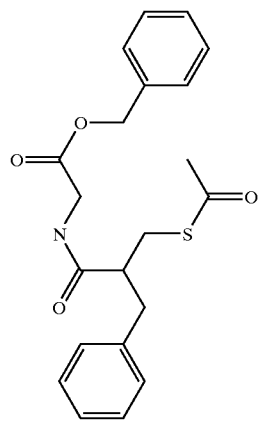
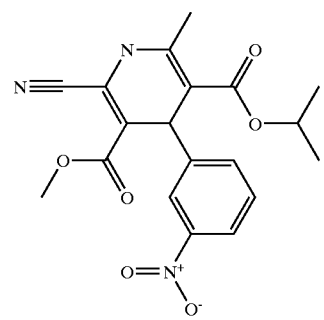
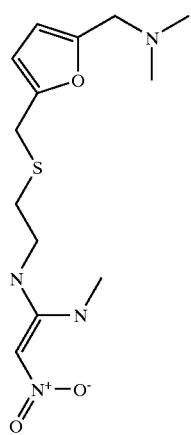
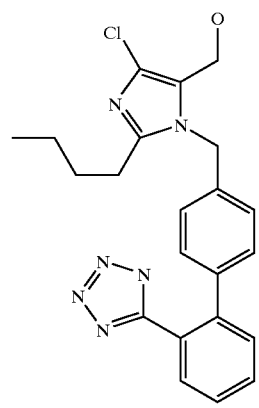
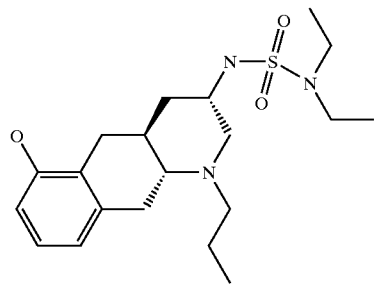
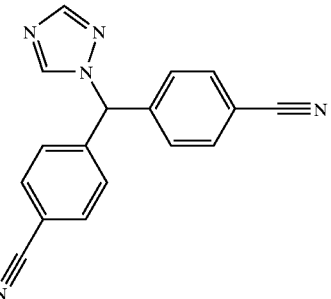
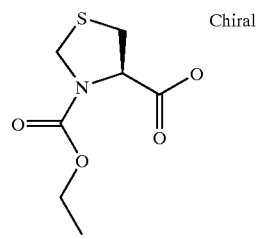
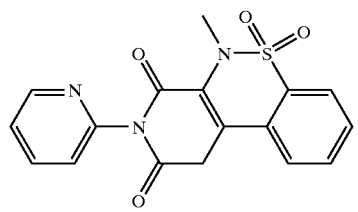
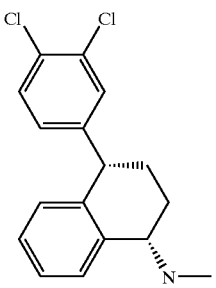
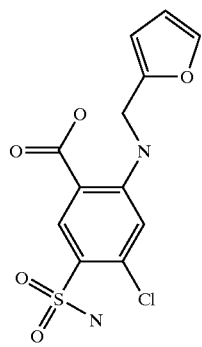

-continued
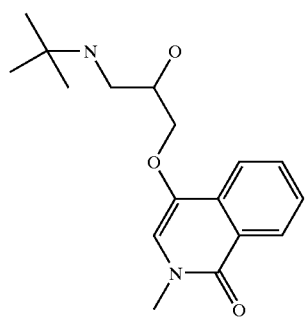 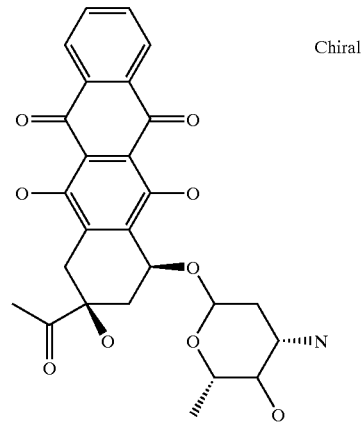 Chiral
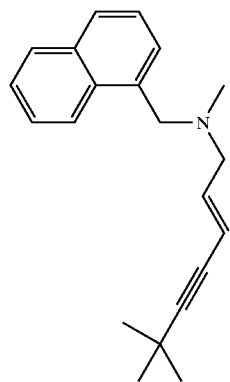 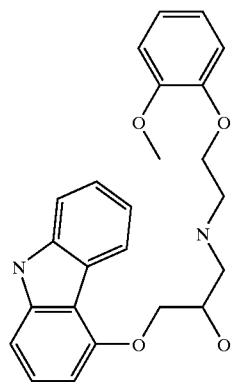 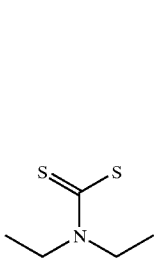 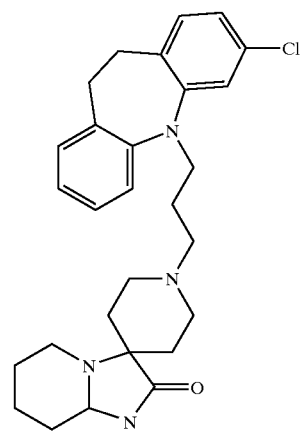
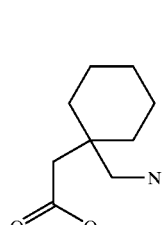 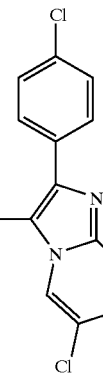 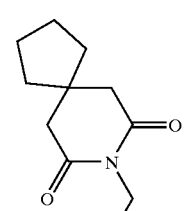 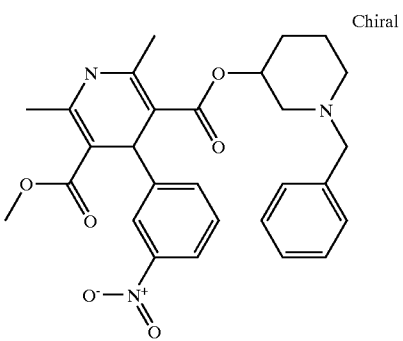 Chiral

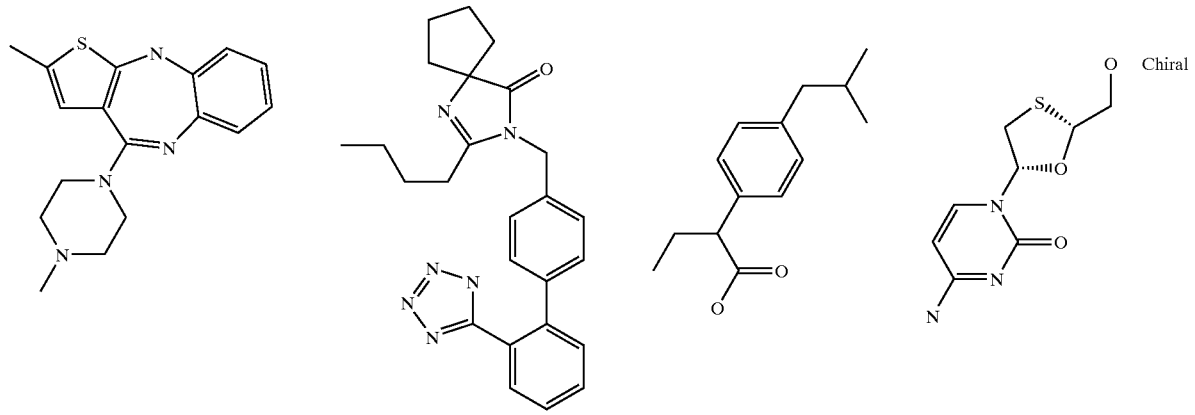
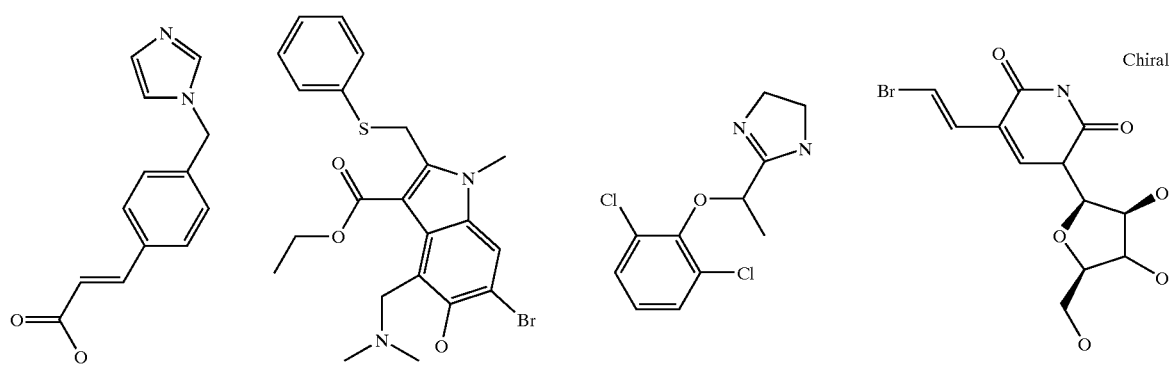
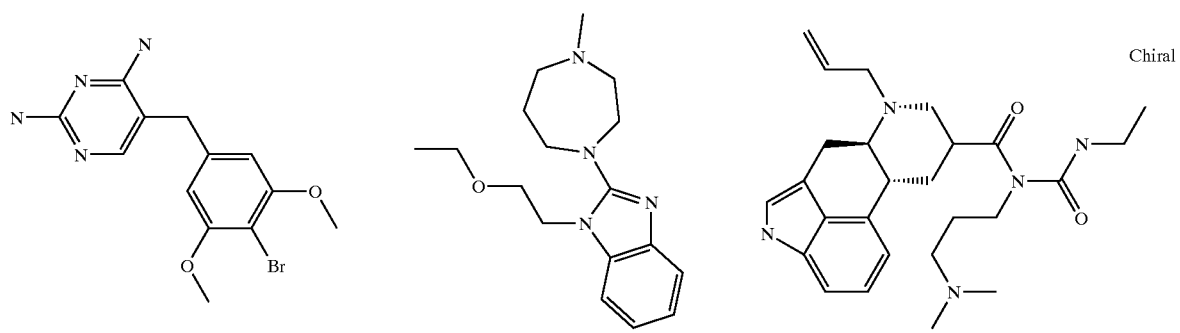
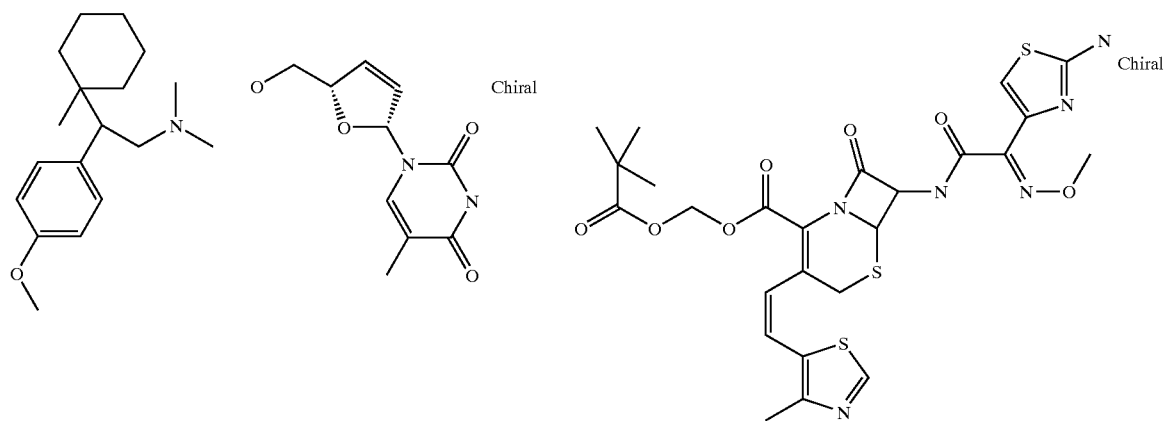

-continued
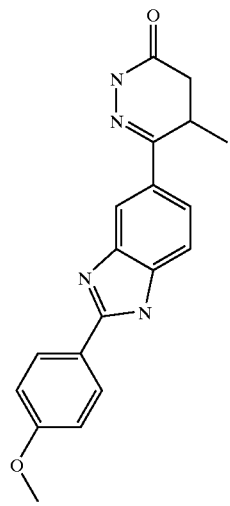 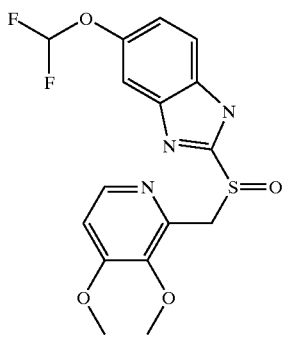 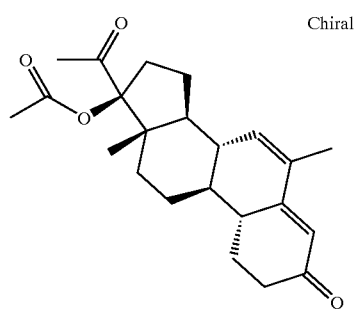
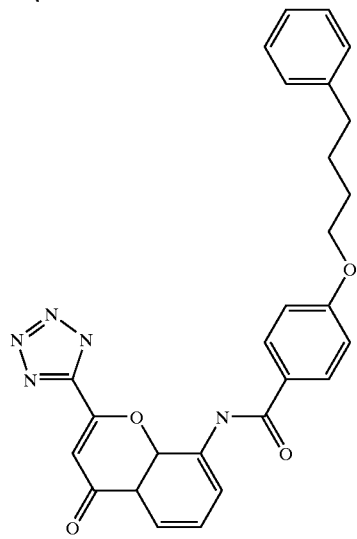 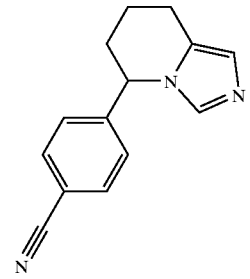 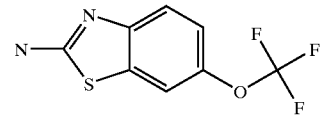
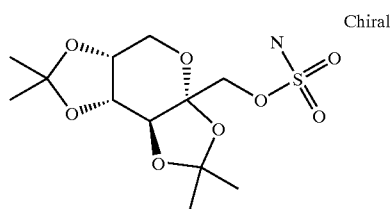 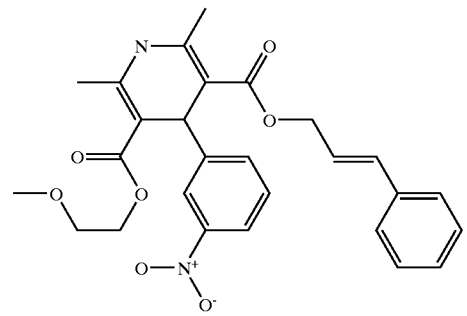 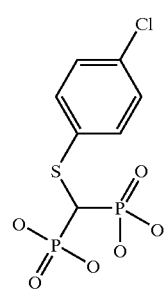
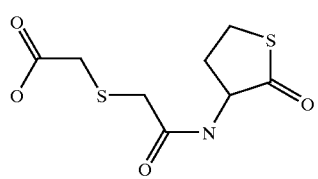 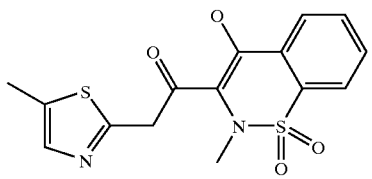 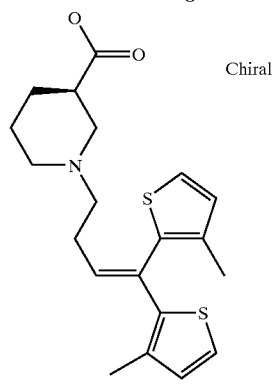

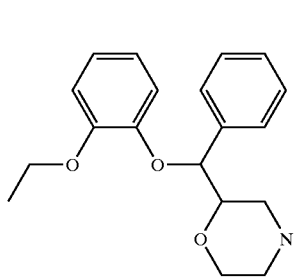 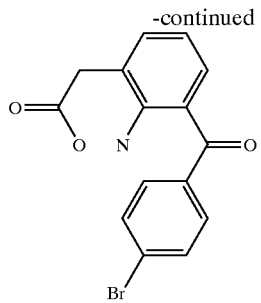 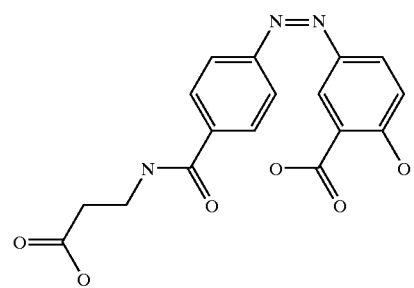

-continued

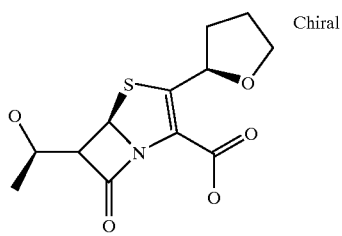 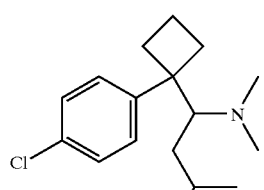 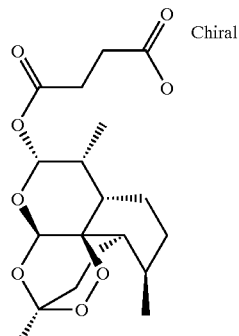

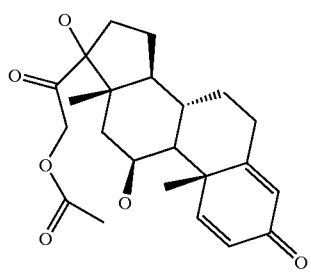 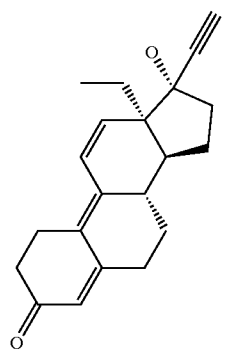 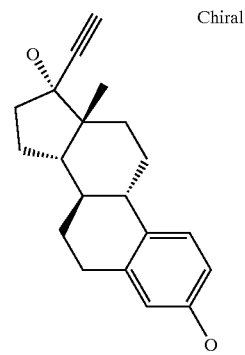

What is claimed is:

1. A method of mapping a chemical structure of a target type into a target hyper-volume within a model in N-dimensional space comprising a plurality of chemical structures, each chemical structure in said model having an associated set of chemical variables defining its position within said N-dimensional space, each chemical variable having a maximum and minimum value within said model, said method comprising the steps of:
   a) storing core chemical structure data representing a plurality of core chemical structures of said target type within said target hyper-volume, said target hyper-volume being positioned away from said maximum and minimum values of said chemical variables;
   b) storing satellite chemical structure data representing a plurality of satellite chemical structures not of said target type positioned outside of said target hyper-volume;
   c) determining from characteristics of said target chemical structure a position of said target chemical structure within said hyper-volume using the same evaluation criteria as used for said core chemical structures and said satellite chemical structures;
   d) positioning said target chemical structure within said model relative to said core chemical structures and said satellite chemical structures in accordance with said determined position; and
   e) generating a user output indicative of said relative position of said target chemical structure.

2. The method as claimed in claim 1, wherein said target type is a pharmaceutically active chemical structure and said core chemical structure is a pharmaceutical.

3. The method as claimed in claim 2, wherein said satellite chemical structures are pharmaceutically inactive.

4. The method as claimed in claim 1, wherein said chemical variables of said target chemical structure are subjected to principal component analysis to determine the position of the target chemical structure within said hyper-volume.

5. The method as claimed in claim 1, wherein chemical variables of said core chemical structures and said satellite chemical structures are subjected to principal component analysis to determine eigen-vectors that serve as axes of said N-dimensional space.

6. The method as claimed in claim 1, wherein if said target chemical structure is found to lie outside of said target hyper-volume, then data representing said target chemical structure may be added to said satellite chemical structure data.

7. The method as claimed in claim 1, wherein said set of chemical variables comprises a variable representing molecular weight.

8. The method as claimed in claim 7, wherein all of said chemical structures within said model have a molecular weight of between 1500 and 30.

9. The method as claimed in claim 7, wherein all of said chemical structures within said model have a molecular weight of between 822 and 60.

10. The method as claimed in claim 1, wherein said set of chemical variables comprises a variable representing molecular size.

11. The method as claimed in claim 10, wherein said variable representing molecular size has a value equivalent to 1 point for every 4 non-hydrogen atoms.

12. The method as claimed in claim 11, wherein all of said chemical structures within said model have a molecular size value of between 50 and 0.

13. The method as claimed in claim 11, wherein all of said chemical structures within said model have a molecular size value of between 14 and 1.

14. The method as claimed in claim 1, wherein said set of chemical variables comprises a variable representing molecular flexibility.

15. The method as claimed in claim 14, wherein said variable representing molecular flexibility is a count representing non-terminal rotatable bonds, repeating units and rings within a molecule.

16. The method as claimed in claim 13, wherein all of said chemical structures within said model have a variable representing molecular flexibility of between 50 and 0.

17. The method as claimed in claim 15, wherein all of said chemical structures within said model have a variable representing molecular flexibility of between 34 and 0.

18. The method as claimed in claim 1, wherein said set of chemical variables comprises a variable representing molecular rigidity.

19. The method as claimed in claim 18, wherein said variable representing molecular rigidity is a count of all rigid structures within a molecule.

20. The method as claimed in claim 19, wherein all of said chemical structures within said model have a variable representing molecular rigidity of between 30 and 0.

21. The method as claimed in claim 19, wherein all of said chemical structures within said model have a variable representing molecular rigidity of between 12 and 0.

22. The method as claimed in claim 1, wherein said set of chemical variables comprises a variable representing the number of formal negative charges on a molecule.

23. The method as claimed in claim 22, wherein all of said chemical structures within said model have a variable representing the number of formal negative charges of between 0 and −4.

24. The method as claimed in claim 1, wherein said set of chemical variables comprises a variable representing the number of formal positive charges on a molecule.

25. The method as claimed in claim 24, wherein all of said chemical structures within said model have a variable representing the number of formal positive charges of between 5 and 0.

26. The method as claimed in claim 1, wherein said set of chemical variables comprises a variable representing the ability of a molecule to accept hydrogen bonds.

27. The method as claimed in claim 26, wherein said variable representing the ability of a molecule to accept hydrogen bonds is a count of the number of oxygen and nitrogen atoms within a molecule that can accept a hydrogen bond.

28. The method as claimed in claim 27, wherein all of said chemical structures within said model have a variable representing the ability of a molecule to accept hydrogen bonds of between 35 and 0.

29. The method as claimed in claim 27, wherein all of said chemical structures within said model have a variable representing the ability of a molecule to accept hydrogen bonds of between 14 and 0.

30. The method as claimed in claim 1, wherein said set of chemical variables comprises a variable representing the ability of a molecule to donate hydrogen bonds.

31. The method as claimed in claim 30, wherein said variable representing the ability of a molecule to donate hydrogen bonds is a count of the number of O—H and N—H moieties within a molecule that can donate a hydrogen to form a hydrogen bond.

32. The method as claimed in claim 31, wherein all of said chemical structures within said model have a variable representing the ability of a molecule to donate hydrogen bonds of between 25 and 0.

33. The method as claimed in claim 31, wherein all of said chemical structures within said model have a variable representing the ability of a molecule to donate hydrogen bonds of between 16 and 0.

34. The method as claimed in claim 1, wherein said set of chemical variables comprises a variable representing the lipophilicity of a molecule.

35. The method as claimed in claim 34, wherein said variable representing lipophilicity represents the partition coefficient for said molecule between octanol and water.

36. The method as claimed in claim 35, wherein all of said chemical structures within said model have a variable representing lipophilicity of between 10 and −10.

37. The method as claimed in claim 1, wherein said set of chemical variables comprises a variable representing the sum of atomic polarizabilities within a molecule.

38. The method as claimed in claim 37, wherein all of said chemical structures within said model have a variable representing the sum of atomic polarizabilities of between 150 and 0.

39. The method as claimed in claim 37, wherein all of said chemical structures within said model have a variable representing the sum of atomic polarizabilities of between 120 and 5.2.

40. The method as claimed in claim 1, wherein said set of chemical variables comprises a variable representing calculated molecular refractivity.

41. The method as claimed in claim 40, wherein all of said chemical structures within said model have a calculated molecular refractivity of between 35 and 0.

42. The method as claimed in claim 1, wherein said set of chemical variables comprises a variable representing molecular volume.

43. The method as claimed in claim 42, wherein all of said chemical structures within said model have a molecular volume of between 2000 and 20 cubic Angstroms.

44. The method as claimed in claim 1, wherein said target hyper-volume is defined by Pfizer's "Rule of 5".

45. The method as claimed in claim 1, wherein one or more anchor chemical structures are situated at the periphery of said target hyper-volume.

46. The method as claimed in claim 45, wherein said anchor chemical structure is a pharmaceutical.

47. A computer apparatus comprising a program for performing the method steps of any of claims 1–46.

48. An apparatus for mapping a target chemical structure of a target type into a target hyper-volume within a model in N-dimensional space comprising a plurality of chemical structures, each chemical structure in said model having an associated set of chemical variables defining its position within said N-dimensional space, each chemical variable having a maximum and minimum value within said model, said apparatus comprising:

a) a memory operable to store core chemical structure data representing a plurality of core chemical structures of said target type within said target hyper-volume, said target hyper-volume being positioned away from said maximum and minimum values of said chemical variables and operable to store satellite chemical structure data representing a plurality of satellite chemical structures not of said target type positioned outside of said target hyper-volume;

b) determination logic operable to determine from characteristics of said target chemical structure a position of said target chemical structure within said hyper-volume using the same evaluation criteria as used for said core chemical structures and said satellite chemical structures;

c) positioning logic operable to position said target chemical structure within said model relative to said core chemical structures and said satellite chemical structures in accordance with said determined position; and d) a user output device for generating a user output indicative of said relative position of said target chemical structure.

49. A method of forming a model in N-dimensional space comprising a plurality of chemical structures and a target hyper-volume into which target chemical structures are to be mapped, said method comprising the steps of:

a) selecting a set of chemical variables defining said N-dimensional space;

b) selecting maximum and minimum values for said chemical variables;

c) selecting a representative set of core chemical structures within said target hyper-volume;

d) selecting a representative set of satellite chemical structures outside of said target hyper-volume; and e) iteratively testing and altering said model to obtain a set of chemical variables, maximum and minimum values, core chemical structures and satellite chemical structures that span said N-dimensional space and that allow target chemical structures to be mapped to within said target hyper-volume.

* * * * *

UNITED STATES PATENT AND TRADEMARK OFFICE
CERTIFICATE OF CORRECTION

PATENT NO. : 6,675,136 B1
DATED : January 6, 2004
INVENTOR(S) : Gottfries et al.

It is certified that error appears in the above-identified patent and that said Letters Patent is hereby corrected as shown below:

Column 73,
Line 22, "claim 13" should read --claim 15 --.

Column 74,
Line 59, "any of" should read -- any one of --.

Signed and Sealed this

Eleventh Day of May, 2004

JON W. DUDAS
*Acting Director of the United States Patent and Trademark Office*